United States Patent [19]

Resnick et al.

[11] Patent Number: 5,580,718
[45] Date of Patent: Dec. 3, 1996

[54] PRIMERS AND PROBES FOR DETECTION OF HEPATITIS C AND NOVEL VARIANTS

[75] Inventors: Robert M. Resnick, Richmond; Karen K. Y. Young, San Ramon, both of Calif.

[73] Assignee: Hoffmann-La Roche Inc., Nutley, N.J.

[21] Appl. No.: 449,626

[22] Filed: May 24, 1995

Related U.S. Application Data

[63] Continuation of Ser. No. 240,547, May 10, 1994, Pat. No. 5,527,669, which is a continuation-in-part of Ser. No. 751,305, Aug. 27, 1991, abandoned, and a continuation of Ser. No. 918,844, Jul. 21, 1992, abandoned.

[51] Int. Cl.$^6$ .............................. C12Q 1/68; C12Q 1/70; C12P 19/34; C07H 21/04
[52] U.S. Cl. ................................ 435/5; 435/6; 435/91.2; 536/24.3; 536/24.32
[58] Field of Search ................................ 435/5, 6, 91.2; 536/24.3–.32

[56] References Cited

U.S. PATENT DOCUMENTS

| | | | |
|---|---|---|---|
| 4,683,195 | 7/1987 | Mullis et al. | 435/6 |
| 4,965,188 | 10/1990 | Gelfand et al. | 435/6 |

FOREIGN PATENT DOCUMENTS

| | | |
|---|---|---|
| 0398748 | 11/1990 | European Pat. Off. . |
| 0419182 | 3/1991 | European Pat. Off. . |
| 0461863 | 12/1991 | European Pat. Off. . |
| 0464287 | 1/1992 | European Pat. Off. . |
| 0468657 | 1/1992 | European Pat. Off. . |
| 0469348 | 2/1992 | European Pat. Off. . |
| 0485209 | 5/1992 | European Pat. Off. . |
| 9109944 | 7/1991 | WIPO . |
| 9202642 | 2/1992 | WIPO . |
| 9203458 | 3/1992 | WIPO . |

OTHER PUBLICATIONS

Saiki et al., 1988, "Diagnosis of Sickle Cell Anemia and B–Thalassemia With Enzymatically Amplified DNA and Nonradioactive Allele–Specific Oligonucleotide Probes" N. Eng. J. Med. 319(9):537 . 541.

Choo et al., 1989, "Isolation of a cDNA Clone Derived From a Blood–Borne Non–A, Non–B viral Hepatitis Genome" Science 244:359–362.

Choo et al., 1991, "Genetic Organization and Diversity of the Hepatitis C Virus" Proc. Natl. Acad. Sci. USA 88:2451–2455.

Kato et al., 1990, "Molecular Cloning of the Human Hepatitis C Virus Genome From Japanese Patients With Non–A, Non–B Hepatitis" Proc. Natl. Acad. Sci. USA 87:9524–9528.

Takamizawa et al., 1991, "Structure and Organization of the Hepatitis C Virus Genome Isolated From Human Carriers" J. Virol. 65(3):1105–1113.

Takeuchi et al., 1990, "Nucleotide Sequence of Core and Envelope Genes of the Hepatitis C Virus Genome Derived Directly From Human Healthy Carriers" Nuc. Acids Res. 18(15):4626.

Maeno et al., 1990, "A cDNA Clone Closely Associated With Non–A, Non–B Hepatitis" Nuc. Acids Res. 18(9):2685–2689.

Okamoto et al., 1991, "Nucleotide Sequence of the Genomic RNA of Hepatitis C Virus Isolated From a Human Carrier: Comparison With Reported Isolates for Conserve and . . . Regions" J. General Virology 72:2697–2704.

Clewley, 1990, "Detection of Hepatitis C Virus RNA in Serum" Lancet 336:309–310.

Enomoto et al., 1990, "There are Two Major Types of Hepatitis C Virus in Japan" biochem. Biophys. Res. Commun. 170(3):1021–1025.

Garson et al., 1990, "Detection of Hepatitis C Viral Sequences in Blood Donations by 'Nested' Polymerase Chain Reaction and Prediction of Infectivity" Lancet 335:1419–1422.

Garson et al., 1990, "Demonstration of Viraemia Patterns in Haemophiliacs Treated With Hepatitis–C–Virus–Contaminated Factor VIII Concentrations" Lancet 336:1022–1025.

Kaneko et al., 1990, "Detection of Serum Hepatitis C Virus RNA" Lancet 335:976.

Kato et al., 1990, "Detection of Hepatitis C Virus Ribonucleic Acid in the Serum by Amplification With Polymerase Chain Reaction" J. Clin. Invest. 86;1764–1767.

Kato et al., 1990, "Sequence Diversity of Hepatitis C Viral Genomes" Mol. Biol. Med. 7:495–501.

Kubo et al., 1989, "A cDNA Fragment of Hepatitis C Virus Isolated From an Implicated Donor of Post–Transfusion Non–A, Non–B Hepatitis in Japan" Nuc. Acids Res. 17(24):10367–10372.

Ohkoshi et al., 1990, "Detection of Hepatitis C Virus RNA in Sera and Liver Tissues of Non–A, Non–B Hepatitis Patients Using the Polymerase Chain Reaction" Jpn. J. Cancer Res. 81:862–865.

Shimizu et al., 1990, "Early Events in Hepatitis C Virus Infection of Chimpanzees" Proc. Natl. Acad. Sci. USA 87:6441–6444.

Simmonds et al., 1990, "Hepatitis C Quantification and Sequencing in Blood Products, Haemophiliacs, and Drug Users" Lancet 336:1469–1472.

Takeuchi et al., 1990, "Hepatitis C Viral cDNA Clones Isolated From a Healthy Carrier Donor Implicated in Post-Transfusion Non–A, Non–B Hepatitis" Gene 91:287–291.

(List continued on next page.)

*Primary Examiner*—Stephanie W. Zitomer
*Assistant Examiner*—Dianne Rees
*Attorney, Agent, or Firm*—George M. Gould; Stacey R. Sias; Douglas A. Petry

[57] ABSTRACT

Oligonucleotides primers can be used to amplify and detect Hepatitis C virus nucleic acids in a process that involves reverse transcription of the viral genomic RNA to create cDNA and the subsequent amplification of the cDNA by the polymerase chain reaction. Oligonucleotide probes can be used to detect the presence of amplified DNA by hybridization. The invention provides improved methods, compositions, and kits for amplifying and detecting U.S., Japan, and HCV-C prototype nucleic acids.

3 Claims, 2 Drawing Sheets

OTHER PUBLICATIONS

Ulrich et al., 1990, "Detection, Semiquantitation, and Genetic Variation in Hepatitis C Virus Sequences Amplified From the Plasma of Blood Donors With Elevated Alanine Aminotransferase" J. Clin. Invest. 86:1609–1614.

Weiner et al., 1990, "Detection of Hepatitis C Viral Sequences in Non–A, Non–B Hepatitis" 335:1–3 Lancet.

Yoneyama et al., 1990, "Detection of Hepatitis C Virus cDNA Sequence by the Polymerase Chain Reaction in Hepatocellular Carcinoma Tissues" Jpn. J. Med. Sci. Biol. 43:89–94.

Zonaro et al., 1991, "Detection of Serum Hepatitis C Virus RNA in Acute Non–A, Non–B Hepatitis" J. Infect. Diseases 163:923–924.

Takeuchi et al., 1990, "The Putative Nucleocapsid and Envelope Protein Genes of Hepatitis C Virus Determined by Comparison of the Nucleotide Sequences of Two Isolates Derived From an Experimentally Infected Chimpanzee and Healthy Human Carriers" J. Gen. Vir. 71:3027–3033.

Okamoto et al., 1990, "The 5'–Terminal Sequence of the Hepatitis C Virus Genome" Japan J. Exp. Med. 60(3):167–177.

Han et al., 1991, "Characterization of the Terminal Regions of Hepatitis C Viral RNA: Identification of Conserved Sequences in the 5'–Untranslated Region of Poly(A) Tails at the 3'End" Proc. Natl. Acad. Sci. USA 88:1711–1715.

Okamoto et al., 1990, "Detection of Hepatitis C Virus RNA by a Two–Stage Polymerase Chain Reaction With Two Pairs of Primers Deduced From the 5'–Noncoding Region" Japan J. Exp. Med. 60(4):215–222.

Kanai et al., 1990, "Suppression of Hepatitis C Virus RNA by Interferon–Alpha" Lancet 336:245.

Garson et al., 1990, "Enhanced Detection by PCR of Hepatitis C Virus RNA" Lancet 336:878–879.

Lee et al., 1992, J. Clin. Microbiology 30(6):1602–1604 "Identification of Hepatitis C Viruses With a Nonconserved Sequence of the 5' Untranslated Region".

Bethesda Research Laboratories Catalogue–Reference Guide (published in 1985 by Bethesda Research Laboratories, Gaitherburg, MD) pp. 52 and 53.

Kato et al., 1989, "Japanese Isolates of the Non–A, Non–B Hepatitis Viral Genome Show Sequence Variations from the Original Isolate in the U.S.A." Proc. Japan Acad. 65(9):219–223 (Ser. B).

Sommer et al., 1989, "Minimal Homology Requirements for PCR Primers" *Nucleic Acids Res.* 17(16):6749.

Matthews et al Analytical Biochemistry 169:1–25, 1988.

Kato et al. PNAS 87:9524–9528, 1990.

Takimazawa et al. J. of Virol. 65:1105–1113.

Enomoto et al. Biochem. Biophys. Res. Comm 170: 1021–1025, 1990.

Figure 1A

Seq. ID Nos.

(Seq. ID No. 29) C 9 5'
(Seq. ID No. 30) R116
(Seq. ID No. 31) R45
(Seq. ID No. 32) R110
(Seq. ID No. 33) R43
                  HCV-J1
                  HCV-J4
                  HCV-J
                  HCV-BK
                  HCV-1 US-PT ACTGTCTTCACGCAGAAAGCGTCTAGCCATGGCGTTAGTATGAGTGTCGTGCAGCCTCCAGGACCCCCCCTCCCGGGAGAGCCATAGTG
                              45

C9
R116
R45
R110
R43
HCV-J1
HCV-J4
HCV-J
HCV-BK
HCV-1 US-PT GTCTGCGGAACCGGTGAGTACACCGGAATTGCCAGGACGACCGGGTCCTTTCTTGGATCAACAACCGCTCAATGCCTGGAGATTTGGGCGTGCCCCCG
            139

C9
R116
R45
R110
R43
HCV-J1
HCV-J4
HCV-J
HCV-BK
HCV-1 US-PT CAAGACTGCTAGCCGAGTAGTGTTGGGTCGCGAAAGGCCTTGTGCCTGTACTGCCTGATAGGGTGCTTGCGAGTGCCCCGGGAGTCTCGTAGACCGTGCACC
            230                                                                                           341

Figure 1B

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CCAAGCTTCA CCATAGATCA CT                                                                             2 2

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGCGACACTC CACCATAGAT CACT                                                                    2 4

( 2 ) INFORMATION FOR SEQ ID NO:3:

( i ) SEQUENCE CHARACTERISTICS:
        ( A ) LENGTH: 31 base pairs
        ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:3:

CCAAGCTTAG ATCACTCCCC TGTGAGGAAC T 31

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:4:

CCAAGCTTCA CGCAGAAAGC GTCTAGCCAT 30

(2) INFORMATION FOR SEQ ID NO:5:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:5:

GCAGAAAGCG TCTAGCCATG GCGT 24

(2) INFORMATION FOR SEQ ID NO:6:

(i) SEQUENCE CHARACTERISTICS:
(A) LENGTH: 26 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:6:

ACGCAGAAAG CGTCTAGCCA TGGCGT 26

(2) INFORMATION FOR SEQ ID NO:7:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:7:

CCTCCAGGAC CCCCCTCCC GGGAGAGCCA 30

(2) INFORMATION FOR SEQ ID NO:8:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: DNA (genomic)

( x i ) SEQUENCE DESCRIPTION: SEQ ID NO:8:

GAGTACACCG GAATTGCCAG GACGACC                                                                 27

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

ACCCGCTCAA TGCCTGGAGA T                                                                       21

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGAAGCTTGC TAGCCGAGTA GT                                                                      22

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CCGCAAGACT GCTAGCCGAG TAGT                                                                    24

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GTTGGGTCGC GAAAGGCCTT GTGGT                                                                   25

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GGTGCTTGCG AGTGCCCCGG GAGGTCTCGT                                                              30

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GACTTCCGAG CGGTCGCAAC CTCG　　　　　　　　　　　　　　　　　　　　　　　　24

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CCCAACACTA CTCGGCTAGC AGTCT　　　　　　　　　　　　　　　　　　　　　　　　25

( 2 ) INFORMATION FOR SEQ ID NO:16:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

AAGGCCTTTC GCGACCCAAC ACTACT　　　　　　　　　　　　　　　　　　　　　　　26

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CACAAGGCCT TTCGCGACCC AACACT　　　　　　　　　　　　　　　　　　　　　　　26

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CTCGCAAGCA CCCTATCAGG CAGT　　　　　　　　　　　　　　　　　　　　　　　　24

( 2 ) INFORMATION FOR SEQ ID NO:19:

( i ) SEQUENCE CHARACTERISTICS:
        ( A ) LENGTH: 26 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

CACTCGCAAG CACCCTATCA GGCAGT 26

( 2 ) INFORMATION FOR SEQ ID NO:20:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

GGGAATTCGC AAGCACCCTA TCAGGCAGT 29

( 2 ) INFORMATION FOR SEQ ID NO:21:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

CGAGGTTGCG ACCGCTCGGA AGT 23

( 2 ) INFORMATION FOR SEQ ID NO:22:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

AGGTTGCGAC CGCTCGGAAG T 21

( 2 ) INFORMATION FOR SEQ ID NO:23:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

AGGTTGCGAC CGCTCGGAAG T 21

( 2 ) INFORMATION FOR SEQ ID NO:24:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

AATGCCATAG AGGGGCCAAG G　　　　　　　　　　　　　　　　　　　　　　　　　　　　21

( 2 ) INFORMATION FOR SEQ ID NO:25:

( i ) SEQUENCE CHARACTERISTICS:
     ( A ) LENGTH: 21 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:25:

ATTGCCATAG AGGGGCCAAG G　　　　　　　　　　　　　　　　　　　　　　　　　　　　21

( 2 ) INFORMATION FOR SEQ ID NO:26:

( i ) SEQUENCE CHARACTERISTICS:
     ( A ) LENGTH: 31 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:26:

CAGAATTCAT TGCCATAGAG GGGCCAAGGA T　　　　　　　　　　　　　　　　　　　　31

( 2 ) INFORMATION FOR SEQ ID NO:27:

( i ) SEQUENCE CHARACTERISTICS:
     ( A ) LENGTH: 22 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:27:

CAGAATTCGC CCTCATTGCC AT　　　　　　　　　　　　　　　　　　　　　　　　　　22

( 2 ) INFORMATION FOR SEQ ID NO:28:

( i ) SEQUENCE CHARACTERISTICS:
     ( A ) LENGTH: 24 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:28:

CCCACCCCAA GCCCTCATTG CCAT　　　　　　　　　　　　　　　　　　　　　　　　24

( 2 ) INFORMATION FOR SEQ ID NO:29:

( i ) SEQUENCE CHARACTERISTICS:
     ( A ) LENGTH: 526 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:29:

ACTGTCTTCA CGCAGAAAGC GTCTAGCCAT GGCGTTAGTA TGAGTGTCGT ACAGCCTCCA　　60

GGCCCCCCCC TCCCGGGAGA GCCATAGTGG TCTGCGGAAC CGGTGAGTAC ACCGGAATTA　120

| CCGGAAAGAC | TGGGTCCTTT | CTTGGATAAA | CCCACTCTGT | GTCCGGTCAT | TTGGGCGTGC | 180 |
| CCCCGCAAGA | CTGCTAGCCG | AGTAGCGTTG | GGTTGCGAAA | GGCCTTGTGG | TACTGCCTGA | 240 |
| TAGGGTGCTT | GCGAGTGCCC | CGGGAGGTCT | CGTAGACCGT | GCATCATGAG | CACAAATCCT | 300 |
| AAACCTCAAA | GAAAAACCAA | AAGAAACACA | AACCGCCGCC | CACAGGACGT | TAAGTTTCCG | 360 |
| GGTGGCGGCC | AGATCGTTGG | CGGAGTTTAC | TTGCTGCCGC | GCAGGGCCC  | CAGGTTGGGT | 420 |
| GTGCGCGCGA | CAAGAAAGAC | TTCCGAGCGA | TCCCAGCCGC | GTGGGAGACG | CCAGCCCATC | 480 |
| CCAAAAGATC | GGCGCTCCAC | CGGCAAGTCC | TGGGGAAAGC | CAGGAT     |            | 526 |

( 2 ) INFORMATION FOR SEQ ID NO:30:

( i ) SEQUENCE CHARACTERISTICS:
        ( A ) LENGTH: 494 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

| GGCGTTAGTA | TGAGTGTCGT | ACAGCCTCCA | GGCCCCCCCC | TCCCGGGAGA | GCCATAGTGG | 60 |
| TCTGCGGAAC | CGGTGAGTAC | GCCGAATTAC | CGGAAAGACT | GGGTCCTTTC | TTGGATAAAC | 120 |
| CCACTCTATG | TCCGGTCATT | TGGGCGTCCC | CCGCAAGACT | GCTAGCCGAG | TAGCGTTGGG | 180 |
| TTGCGAAAGG | CCTTGTGGTA | CTGCCTGATA | GGGTGCTTGC | GAGTGCCCCG | GAGGTCTCG  | 240 |
| TAGACCGTGC | ATCATGAGCA | CAGATCCTAA | ACCTCAAAGA | AAAACCAAAA | GAAATACAAA | 300 |
| CCGCCGCCCA | CAGGACGTCA | AGTTCCCGGG | TGGCGGCCAG | ATCGTTGGCG | GAGTTTACTT | 360 |
| GCTGCCGCGC | AGGGGCCCCA | GGTTGGGTGT | GCGCACAACA | AGGAAGACTT | CCGAGCGATC | 420 |
| CCAGCCGCGT | GGAAGACGCC | AGCCCATCCC | GAAAGATCGG | CGCTCCACCG | GTAAGTCCTG | 480 |
| GGGAAAGCCA | GGAT       |            |            |            |            | 494 |

( 2 ) INFORMATION FOR SEQ ID NO:31:

( i ) SEQUENCE CHARACTERISTICS:
        ( A ) LENGTH: 494 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

| GGCGTTAGTA | TGAGTGTCGT | ACAGCCTCCA | GGCCCCCCCC | TCCCGGGAGA | GCCATAGTGG | 60 |
| TCTGCGGAAC | CGGTGAGTAC | GCCGAATTGC | CGGAAAGACT | GGGTCCTTTC | TTGGATAAAC | 120 |
| CCACTCTATG | TCCGGTCATT | TGGGCGTCCC | CCGCAAGACT | GCTAGCCGAG | TAGCGTTGGG | 180 |
| TTGCGAAAGG | CCTTGTGGTA | CTGCCTGATA | GGGTGCTTGC | GAGTGCCCAG | GAGGTCTCG  | 240 |
| TAGACCGTGC | ATCATGAGCA | CAAATCCTAA | ACCCCAAAGA | AAAACCAAAA | GAAACACAAA | 300 |
| CCGCCGCCCA | CAGGACGTTA | AGTTCCCGGG | TGGCGGCCAG | ATCGTTGGCG | GAGTTTACTT | 360 |
| GATGCCGCGC | AGGGGCCCCA | GGTTGGGTGT | GCGCGCGACG | AGGAAGACTT | CCGAGCGATC | 420 |
| CCAGCCGCGT | GGGAGACGCC | AGCCCATCCC | GAAAGATCGG | CGTTCCACCG | GCAAGTCCTG | 480 |
| GGGAAAGCCA | GGAT       |            |            |            |            | 494 |

( 2 ) INFORMATION FOR SEQ ID NO:32:

( i ) SEQUENCE CHARACTERISTICS:
  ( A ) LENGTH: 494 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:32:

| | | | | | |
|---|---|---|---|---|---|
| GGCGTTAGTA | TGAGTGTCGT | ACAGCCTCCA | GGCCCCCCCC | TCCCGGGAGA | GCCATAGTGG | 60 |
| TCTGCGGAAC | CGGTGAGTAC | GCCGAATTGC | CGGAAAGACT | GGGTCCTTTC | TTGGATTAAC | 120 |
| CCACTCTATG | TCCGGTCATT | TGGGCGTCCC | CCGCAAGACT | GCTAGCCTAG | TAGCGTTGGG | 180 |
| TTGCGAACGG | CCTTGTGGTA | CTGCCTGATA | GGGTGCTTGC | GAGTGCCCCG | GGAGGTCTCG | 240 |
| TAGACCGTGC | ATCATGAGCA | CAAATCCTAA | ACCTCAAAGA | AAAACCAAAA | GAAACACAAA | 300 |
| CCGCCGCCCA | CAGGACGTCA | AGTTCCCGGG | AGGCGGTCAG | ATCGTTGGCG | GAGTTTACTT | 360 |
| GCTGCCGCGC | AGGGGCCCCA | GGTTGGGTGT | GCGCGCGACA | AGGAAGACTT | CCGAGCGATC | 420 |
| CCAGCCGCGT | GGGAGACGCC | AGCCCATCCC | GAAAGATCGG | CGCTCCACCG | GCAAGTCCTG | 480 |
| GGGAAAGCCA | GGAT | | | | | 494 |

( 2 ) INFORMATION FOR SEQ ID NO:33:

( i ) SEQUENCE CHARACTERISTICS:
    ( A ) LENGTH: 494 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:33:

| | | | | | |
|---|---|---|---|---|---|
| GGCGTTAGTA | TGAGTGTCGT | ACAGCCTCCA | GGCCCCCCCC | TCCCGGGAGA | GCCATAGTGG | 60 |
| TCTGCGGAAC | CGGTGAGTAC | ACCGAATTAC | CGGAAAGACT | GGGTCCTTTC | TTGGATAAAC | 120 |
| CCACTCTATG | TCCGGTCATT | TGGGCGTCCC | CCGCAAGACT | GCTAGCCTAG | TAGCGTTGGG | 180 |
| TTGCGAACGG | CCTTGTGGTA | CTGCCTGATA | GGGTGCTTGC | GAGTGCCCCG | GGAGGTCTCG | 240 |
| TAGACCGTGC | ATCATGAGCA | CAAATCCTAA | ACCTCAAAGA | AAAACCAAAA | GAAACACAAA | 300 |
| CCGCCGCCCA | CAGGACGTCA | AGTTCCCGGG | TGGCGGCCAG | ATCGTTGGCG | GAGTTTACTT | 360 |
| GCTGCCGCGC | AGGGGCCCCA | GGTTGGGTGT | GCGCGCGACA | AGGAAGACTT | CCGAACGGTC | 420 |
| CCAGCCGCGT | GGGAGGCGCC | AGCCCATCCC | AAAAGATCGG | CGCTCCACCG | GCAAGTCCTG | 480 |
| GGGAAAGCCA | GGAT | | | | | 494 |

( 2 ) INFORMATION FOR SEQ ID NO:34:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:34:

TTGCCGGAAA GACTGGGTCC TTTC                    24

( 2 ) INFORMATION FOR SEQ ID NO:35:

( i ) SEQUENCE CHARACTERISTICS:
    ( A ) LENGTH: 24 base pairs
    ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:35:

CAAAAGAAAC ACAAACCGCC GCCC 24

(2) INFORMATION FOR SEQ ID NO:36:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:36:

CCAGCCCATC CCGAAAGATC GGCG 24

(2) INFORMATION FOR SEQ ID NO:37:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:37:

TGTCCGGTCA TTTGGGCG 18

(2) INFORMATION FOR SEQ ID NO:38:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:38:

AAACCCACTC TATGTCCGGT C 21

(2) INFORMATION FOR SEQ ID NO:39:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:39:

GTACGCCGGA ATTGCCGGAA A 21

(2) INFORMATION FOR SEQ ID NO:40:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(  x i  ) SEQUENCE DESCRIPTION: SEQ ID NO:40:

CCTCAAAGAA AAACCAAAAG A                                                                                               2 1

( 2 ) INFORMATION FOR SEQ ID NO:41:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

TGGCGTCTCC CACGCGGCTG G                                                                                               2 1

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

CTTTCCCCAG GACCTGCCGG T                                                                                               2 1

( 2 ) INFORMATION FOR SEQ ID NO:43:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

CATAGTGGTC TGCGGAACCG GTGAGT                                                                                          2 6

PRIMERS AND PROBES FOR DETECTION OF HEPATITIS C AND NOVEL VARIANTS

This application is a continuation, of application Ser. No. 08/240,547, filed May 10, 1994, now U.S. Pat. No. 5,527, 669, which is a continuation-in-part of application Ser. No. 07/751,305 filed Aug. 27, 1991 now abandoned and is a continuation of application Ser. No. 07/918,844 filed Jul. 21, 1992 now abandoned.

BACKGROUND OF THE INVENTION

1. Field of the Invention

The present invention provides improved methods and reagents for the detection of Hepatitis C virus, a causative agent of non-A, non-B hepatitis. The reagents include oligonucleotide primers for both reverse transcription of the viral RNA genome and subsequent amplification by the polymerase chain reaction of the cDNA so produced. Sequence specific oligonucleotide probes are provided for the detection of amplified HCV nucleic acid sequences. The primers and probes are useful in a diagnostic test for the detection of HCV infection. This diagnostic test has important applications in both clinical and epidemiological settings.

2. Description of Related Art

Hepatitis C virus (HCV) is one of an unknown number of agents responsible for non-A, non-B hepatitis (NANBH). The prototypical HCV was identified from a eDNA clone of a blood-borne NANBH virus obtained from the plasma of an infected chimpanzee as reported in Choo et al., 1989, *Science* 244:359–362. Nucleotide sequences of genes from this prototype HCV are described in European Patent Publication Nos. 318,216: 388,232; and 398,748. The nucleotide sequence of the HCV genome was reported and compared to related virus in Choo et al., 1991, *Proc. Natl. Acad. Sci. USA* 88:2451–2455.

Sequences from other strains have since been reported. The genome of HCV exhibits a large degree of nucleic acid sequence heterogeneity between isolates. The isolation of cDNA from the HCV RNA genome was reported in Kubo et al., 1989, *Nuc. Acids Res.* 17: 10367–10372. The authors constructed a reverse transcription primer based on the sequence reported in Choo et al., 1989, supra. The fragment of the HCV genome isolated showed 79.8% homology with the prototype HCV sequence. Obtained by a similar protocol, sequences from three different regions were reported in Takeuchi et al., 1990, *Gene* 91:287–291. Sequence homology with the prototype sequence was reported as low as 73.5% for one of the regions.

The HCV genomic sequence from a strain isolated from Japanese patients was reported in Kato et al., 1990, *Proc. Natl. Acad. Sci. USA* 87:9524–9528. The sequence showed 77.4% homology with the prototype HCV genome over the region compared. A sequence for the entire coding region of the HCV genome reported in Takamizawa et al., 1991, *J. Virol.* 65 (3):1105–1113 showed 77% homology with the prototype HCV strain.

In Japan, two main strains, designated strains K1 and K2, have been observed based on a 400 nucleotide region of the genome. These strains have sequence homology with the prototype HCV sequence as low as 67% (see Enomoto et al., 1990, *Biochem. Biophys. Res. Commun.* 170(3):1021–1025). The K2 strain could be further subdivided into two groups, designated Ka and Kb, with about 20% nucleotide variation between the groups and about 5% nucleotide variation within each group.

Similar levels of homology with the prototype HCV sequence were reported in Kato et al., 1990, *J. Clin. Invest.* 86:1764–1767. From 15 patients, cDNA segments were amplified and sequenced. The amplified portion, 37 nucleotides corresponding to positions 3525–3561 in the prototype sequence, showed 68–78% homology with the prototype HCV sequence.

HCV genomic RNA can be detected in sera by creating cDNA from the genomic RNA, amplifying the cDNA with the polymerase chain reaction, and subsequently probing with sequence-specific oligonucleotides. Because of the sequence heterogeneity among HCV strains, primers and probes are likely to be strain-specific, unless a region in which the sequence is conserved across strains can be found. One such conserved region is at the 5'-end of the HCV genome.

The 5'-terminal noncoding sequence of the HCV genome was first reported in Okamoto et al., 1990, *Japan J. Exp. Med.* 60(3):167–177. Comparison between two strains suggested that the 5'-terminal noncoding sequence is conserved. The conserved nature of the 5'-terminal noncoding sequence of the HCV genome was also reported in Hah et al., 1991, *Proc. Natl. Acad. Sci. USA* 88:1711–1715. Partial sequences of a 341 nucleotide region obtained from 11 HCV isolates collected from individuals from five continents were compared. Seven sequences showed complete homology with the prototype sequence; the remaining four showed between one and five base mismatches.

In Okamoto et al., 1990, *Japan J. Exp. Med.* 60(3):215–222, primers for various regions of the HCV genome, including the conserved 5' noncoding region were described. The primers selected from conserved regions successfully amplified nucleic acid from most of the strains tested; primers chosen from heterogeneous regions amplified nucleic acid from a smaller subset of strains. However, the amplification efficiency with these primers was low. The reference describes a two-stage PCR amplification; the second round of amplification was performed on the previously amplified target region using a second set of primers nested within the region amplified by the first set of primers.

A PCR amplification requiring two rounds of amplification using two sets of primers was also reported in Garson et al., 1990, *Lancet* 335:1419–1422. A region encoding a nonstructural protein (NSS) was amplified. Due to sequence heterogeneity, there are HCV sequences not recognized by these primers (see Garson et al., 1990, *Lancet* 336:878–879). Consequently, primers in the conserved 5' noncoding region were tried, but to obtain sufficient sensitivity, a two-sage amplification using sets of nested primers was still necessary. Amplification of the 5'-terminal region using a two-stage amplification with nested primers was also reported in Kanai et al., 1990, *Lancet* 336:245.

Amplification using two rounds of amplification with nested primers is not only inefficient but also greatly increases the probability of contamination. The problems of contamination are well known in the art; opening the reaction tube to change primers and add reagents between amplification steps is best avoided if at all possible. The contamination problem is further aggravated by the need to change reaction conditions between the initial reverse transcription step and the subsequent PCR amplification.

There is still a need for primer oligonucleotides for amplifying HCV sequences, each chosen from a conserved region so that all, or almost all, strains will be amplified, and amplification methods efficient enough that amplification with one set of primers is sufficient. There is also a need for probe oligonucleotides for the detection of the amplified cDNA chosen from a conserved region in between the two conserved regions to which the primers hybridize. Reaction protocol and reagents are needed that allow reverse transcription and PCR to occur using the same reagents, thereby eliminating the need to open the reaction tube during the amplification process.

Moreover, ten percent of NANBH cases are nonreactive with the prototype capsid and envelope antigens. Chaudhary et al., 1991 *J. Clinical Microbiology* 29:2329–2330 and Hosein et al., 1991, *PNAS* 8:3647–3651. Thus, the development of PCR based diagnostics and antigens encoded by new isolates will improve the dependability of serologically based diagnostic tests. The present invention meets these needs by providing primers, probes, and methods for detecting HCV.

SUMMARY OF THE INVENTION

The present invention provides improved methods and reagents for the detection of Hepatitis C virus, a causative agent of non-A, non-B hepatitis. The specific primers and sequence specific oligonucleotide probes provided can be used in a homogeneous reverse transcription-polymerase chain reaction (RT-PCR) that enables amplification and detection of the viral RNA genomic sequences. The efficiency of amplification using the primers and methods of the present invention eliminates the need for a second round of PCR amplification with nested primers, and the high sensitivity of the resulting test provides reliable detection of the nucleic acid.

One aspect of the invention relates to specific oligonucleotide primers. The invention provides compositions comprising an oligonucleotide primer for amplifying an HCV nucleic acid wherein said primer is suitable for amplifying a nucleic acid subsequence from an HCV strain or isotype selected from the group consisting of Japan, U.S. and C9 strains. The primers provided function both in the reverse-transcription of the viral RNA genome and the subsequent amplification of the cDNA produced using the polymerase chain reaction. The primers hybridize to sequences from conserved regions of the HCV genome and, therefore, bind to a variety of strains. The efficiency of amplification using the provided primers is sufficient to eliminate the need for a second round of PCR amplification with nested primers.

Another aspect of the invention relates to probes capable of detecting the presence of HCV genomic nucleic acid regardless of the strain. The probes are complementary to regions conserved across strains. Diagnostic tests using the probes of the present invention can detect a large number of HCV strains without compromising specificity. Thus, the invention provides compositions comprising an oligonucleotide probe for detecting the presence of Hepatitis C virus nucleic acids, wherein the probe is suitable for detecting the nucleic acid of an HCV strain or variant strain selected from the group consisting of Japan, U.S., and C9 prototype strains.

A third aspect of the invention relates to kits. These kits take a variety of forms and can comprise one or more reverse-transcription, amplification, or detection reagents, e.g., primers, probes, polymerases, glycosylases, buffers, and nucleoside triphosphates.

In one embodiment, the invention provides a kit for the detection of nucleic acid specific to a C9 isolate of hepatitis virus, the kit comprising a compartment which contains a nucleic acid probe which binds substantially to a nucleic acid subsequence of the HCV-C9 virus.

Another aspect of the invention relates to methods for amplifying and detecting HCV RNA.

In addition, the present invention relates to compositions comprising a viral nucleic acid sequence substantially homologous to SEQ ID. NO. 29. A cDNA clone, pHCV-C9, containing such a viral sequence, termed here the C9 isolate, is deposited with the American Type Culture Collection and has Deposit No. 75265

The invention also provides oligonucleotide probes and primers for detecting a nucleic acid sequence specific to the C9 isolate and related variants. The probes of the invention preferably comprise a subsequence selected from the following group:

| SEQ ID NO. 34 | 5'-TTGCCGGAAAGACTGGGTCCTTTC-3' | (nt174–197) |
| SEQ ID NO. 35 | 5'-CAAAAGAAACACAAACCGCCGCCC-3' | (nt374–397) |
| SEQ ID NO. 36 | 5'-CCAGCCCATCCCGAAAGATCGGCG-3' | (nt527–550) |
| SEQ ID NO. 37 | (MY160) 5'-TGTCCGGTCATTTGGGCG-3' | (nt216–233) |

The invention further provides oligonucleotide primers for the amplification of nucleic acid sequences specific to a C9 isolate. Primers of the invention for specifically amplifying the C9 variant and related isolates preferably comprise a nucleic acid sequence selected from the following group of upstream primers:

| SEQ ID NO. 38 | 5'-AAACCCACTCTATGTCCGGTC-3' | (nt204–224); |
| SEQ ID NO. 39 | 5'-GTACGCCGGAATTGCCGGAAA-3' | (nt163–183); and |
| SEQ ID NO. 40 | 5'-CCTCAAAGAAAACCAAAAGA-3' | (nt360–380); | for use with one of the following downstream primers:

| SEQ ID NO. 41 | 5'-TGGCGTCTCCCACGCGGCTGG-3' | (nt509–529); and |
| SEQ ID NO. 42 | 5'-CTTTCCCCAGGACCTGCCGGT-3' | (nt555–575). |

The invention also provides probes which substantially bind sequences of the C9 isolate and previously identified Hepatitis C isolates. Preferred probes of this category include:

| SEQ ID NO. 43 | KY150 | 5'-CAT AGT GGT CT GCGGAACCGGT GAGT-3'. |
|---|---|---|

The invention further provides probes for detecting non-C9 HCV sequences.

The invention provides a process for detecting the presence of Hepatitis C genomic nucleic acid, wherein said Hepatitis C genomic nucleic acid is selected from the group consisting of Japan, U.S., and C9 prototype stains, comprising: (a) amplifying a subsequence of the nucleic acid; (b) mixing the amplified nucleic acid with an oligonucleotide probe specific to the subsequence under conditions wherein the probe binds to the subsequence to form a stable hybrid duplex; and (c) detecting hybrids formed between the subsequence and the probe. comprise the following steps:

In another embodiment, the invention provides a process for detecting a C9 isolate of hepatitis virus the method comprising the steps of: (a) contacting a sample suspected of containing an HCV-C9 nucleic acid sequence with a nucleic acid probe having a subsequence complementary to an HCV-C9 nucleic acid sequence; and (b) detecting the hybridization of the probe to said sequence.

The method may further comprise, before step (a), the step of amplifying a subsequence of the sequence specific to the virus. Amplification is preferably achieved by the use the polymerase chain reaction method. The primers and probes above are preferably used in the methods of the invention.

The invention also provides kits for the detection of nucleic acid specific to a C9 isolate of hepatitis virus. The kit comprises a compartment which contains a nucleic acid probe which binds substantially to a nucleic acid subsequence of the nucleic acid sequence. The probe is preferably selected from the group listed above.

Alternate assay methods are based on immunological reactions, such as the reaction of serum antibodies with proteins or viral lysates from C9 isolate or the reaction of immunoglobulins raised against vital antigens with a biological sample containing the virus. The invention thus provides biologically pure immunoglobulins raised against the C9 isolate. The immunoglobulins are preferably a monoclonal antibodies.

To aid in understanding the invention, several terms are defined below.

"Amplification reaction mixture" refers to an aqueous solution comprising the various reagents used to amplify a target nucleic acid. These include: enzymes, aqueous buffers, salts, target nucleic acid, and deoxynucleoside triphosphates. Depending upon the context, the mixture can be either a complete or incomplete amplification reaction mixture.

"Amplification reaction system" refers to any *in vitro* means for multiplying the copies of a target sequence of nucleic acid. Such methods include, but are not limited to, polymerase chain reaction amplification (PCR), DNA ligase, QB RNA replicase, and RNA transcription-based amplification systems. These involve multiple amplification reagents and are more fully described below.

"Amplification reaction tube(s)" refers to a container suitable for holding the amplification reagents. Generally, the tube is constructed of inert components so as to not inhibit or interfere with the amplification system being used.

Where the system requires thermal cycling of repeated heating and cooling, the tube must be able to withstand the cycling process and, typically, precisely fit the wells of the thermocycler.

"Amplification reagents" refer to the various buffers, enzymes, primers, deoxynucleoside triphosphates (both conventional and unconventional), and primers used to perform the selected amplification procedure.

"Amplifying" or "Amplification", which typically refers to an "exponential" increase in target nucleic acid, is being used herein to describe both linear and exponential increases in the numbers of a select target sequence of nucleic acid.

"Bind(s) substantially" refers to complementary hybridization between an oligonucleotide and a target sequence and embraces minor mismatches that can be accommodated by reducing the stringency of the hybridization media to achieve the desired priming for the PCR polymerases or detection of hybridization signal.

The phrase "biologically pure" refers to material that is substantially or essentially free from components which normally accompany it as found in its native state. For instance, affinity purified antibodies or monoclonal antibodies exist in a biologically purified state.

"Hybridizing" refers the binding of two single stranded nucleic acids via complementary base pairing.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

"Nucleotide polymerases" refers to enzymes able to catalyze the synthesis of DNA or RNA from nucleoside triphosphate precursors. In the amplification reactions of this invention, the polymerases are template-dependent and typically add nucleotides to the 3'-end of the polymer being formed. It is most preferred that the polymerase is thermostable as described in U.S. Pat. Nos. 4,889,818 and 5,079,352.

The term "oligonucleotide" refers to a molecule comprised of two or more deoxyribonucleotides or ribonucleotides, such as primers, probes, nucleic acid fragments to be detected, and nucleic acid controls. The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol* 68:90–99; the phosphodiester method of Brown et al, 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 25 nucleotides. Short primer molecules generally require cooler temperatures to form sufficiently stable hybrid complexes with the template. A primer need not reflect the exact sequence of the template but must be sufficiently complementary to hybridize with a template.

In the disclosed embodiments of the invention, sequence specific primers and probes are provided. It will be apparent to those of skill in the art that, provided with those embodiments, additional sequence specific primers and probes can be prepared by, for example, the addition of nucleotides to either the 5' or 3'0 ends, which nucleotides are complementary to the target sequence or are uncomplementary to the target sequence. So long as primer compositions serve as a point of initiation for extension on the target sequences, and so long as the primers and probes comprise at least 14 consecutive nucleotides contained within those exemplified embodiments, such compositions are within the scope of the invention.

The term "primer" may refer to more than one primer, particularly in the case where there is some ambiguity in the information regarding one or both ends of the target region to be amplified. For instance, if a region shows significant levels of polymorphism in a population, mixtures of primers can be prepared that will amplify alternate sequences. A primer can be labeled, if desired, by incorporating a label detectable by spectroscopic, photochemical, biochemical, immunochemical, or chemical means. For example, useful labels include $^{32}$P, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support.

"Probe" refers to an oligonucleotide which binds through complementary base pairing to a subsequence of a target nucleic acid. It will be understood by one of skill in the art that probes will typically substantially bind target sequences lacking complete complementarity with the probe sequence depending upon the stringency of the hybridization conditions. The probes are preferably directly labelled as with isotopes or indirectly labelled such as with biotin to which a streptavidin complex may later bind. By assaying for the presence or absence of the probe, one can detect the presence or absence of the target.

"Recombinant" when referring to a nucleic acid probe refers to an oligonucleotide which is free of native proteins and nucleic acid typically associated with probes isolated from the cell, which naturally contains the probe sequence as a part of its native genome. Recombinant probes include those made by amplification means such as PCR and genetic cloning methods where bacteria are transformed with the recombinant probe.

The term "reverse transcriptase" refers to an enzyme that catalyzes the polymerization of deoxyribonucleoside triphosphates to form primer extension products that are complementary to a ribonucleic acid template. The enzyme initiates synthesis at the 3'-end of the primer and proceeds toward the 5'-end of the template until synthesis terminates. Examples of suitable polymerizing agents that convert the RNA target sequence into a complementary, copy-DNA (cDNA) sequence are avian myeloblastosis virus reverse transcriptase and *Thermus thermophilus* DNA polymerase, a thermostable DNA polymerase with reverse transcriptase activity marketed by Perkin Elmer.

The terms "sequence-specific oligonucleotide" and "SSO" refer to oligonucleotides that have a sequence, called a "hybridizing region," exactly complementary to the sequence to be detected, typically sequences characteristic of a particular allele or variant, which under "sequence-specific, stringent hybridization conditions" will hybridize only to that exact complementary target sequence. Relaxing the stringency of be hybridizing conditions will allow sequence mismatches to be tolerated; the degree of mismatch tolerated can be controlled by suitable adjustment of the hybridization conditions. Depending on the sequences being analyze, one or more sequence-specific oligonucleotides may be employed. The terms "probe" and "SSO probe" are used interchangeably with SSO.

A "sequence specific to" a particular viral isolate is a sequence unique to the isolate, that is, not shared by other previously characterized isolates. A probe containing a subsequence complementary to a sequence specific to an isolate will typically not hybridize to the corresponding portion of the genome of other isolates under stringent conditions (e.g., washing the solid support in 2×SSC, 0.1% SDS at 70° C.).

An antigen or epitope specific to a particular isolate is one that is unique to the isolate and is not shared by other previously characterized isolates. An immunoglobulin raised against the antigen or epitope will not cross react with antigens on previously characterized isolates in standard assays, such as ELISA.

The term "substantially identical" indicates that two or more nucleotide sequences share a majority of their sequence. Generally, this will be at least about 90% of their sequence and preferably about 95% of their sequence. Another indication that sequences are substantially identical is if they hybridize to the same nucleotide sequence under stringent conditions (see, e.g., Sambrook et al., *Molecular Cloning—A Laboratory Manual*, Cold Spring Harbor Laboratory, Cold Spring Harbor, New York, 1985). Stringent conditions are sequence-dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

"Subsequence" refers to a sequence of nucleic acids that comprise a part of a longer sequence of nucleic acids.

The term "target region" refers to a region of a nucleic acid to be analyzed and can include a polymorphic region.

The term "thermostable polymerase enzyme" refers to an enzyme that is relatively stable to heat and catalyzes the polymerization of nucleoside triphosphates to form primer extension products that are complementary to one of the nucleic acid strands of the target sequence. The enzyme initiates synthesis at the 3'-end of the primer and proceeds toward the 5'-end of the template until synthesis terminates. A purified thermostable polymerase enzyme is described more fully in U.S. Pat. No. 4,889,818, incorporated herein by reference, and is developed and manufactured by Hoffmann-La Roche Inc. and commercially available from Perkin Elmer (Norwalk, CT).

BRIEF DESCRIPTION OF THE DRAWINGS

FIG. 1A,B provides an alignment of the novel variant HPV sequence C9, four related variants, and the prototype Japan and U.S. HCV isolates.

DETAILED DESCRIPTION OF THE INVENTION

The Hepatitis C virus is a small RNA virus containing a single, positive sense, molecule of RNA about 10,000 nucleotides in length. The genome contains a single, long, open reading frame believed to be translated into a single, large polyprotein and subsequently processed. The open reading frame begins at nucleotide 343 (using the numbering system from the prototype virus) following an untranslated region (UTR). The 5' UTR sequence is relatively conserved and may be important in vital replication and regulation. The 5'-end of the coding region is also conserved. Certain primers and probes of the present invention hybridize to the conserved region at the 5'-end of the HCV genome.

The oligonucleotide sequences of the hybridizing regions of the primers and probes of the invention are presented below. Those skilled in the art will realize that an oligonucleotide sequence used as the hybridizing region of a primer can also be used as the hybridizing region of a probe. Suitability of a primer sequence for use as a probe depends on the hybridization characteristics of the primer. Similarly, an oligonucleotide used as a probe can be used as a primer.

The oligonucleotides shown in Table 1 are positive sense (upstream) primers or probes. The listing is in order based on the position of the 3'-end of the oligonucleotide when hybridized to genomic nucleic acid. The oligonucleotides that hybridize closest to the 5'-end of the genome are listed first.

product when one of these oligonucleotides is used as a primer. Initial hybridization conditions are chosen such that the base pair mismatches around the restriction site are tolerated. Mismatches near the 5'-end are tolerated better than those near the 3'-end of a primer. The oligonucleotides KY65 (SEQ ID NO. 1), KY98 (SEQ ID NO. 3), KY96 (SEQ ID NO. 4), and KY67 (SEQ ID NO. 10) are upstream primers and contain a HindIII site. The oligonucleotides KY95 (SEQ ID NO. 20), KY99 (SEQ ID NO. 26), and KY68 (SEQ ID NO. 27) are downstream primers and contain an EcoRI site. The incorporation of such restriction sites into the amplified product facilitates cloning of the amplified product.

The present invention also provides a new HCV isolate. Most isolates are related to one of two strains of HCV. The first is a U.S. prototype strain described in European Publication Nos. 318,216 (published May 31, 1989), 388,232 (published September 19, 1990), and 398,748 (published November 22, 1990). The second is a Japanese strain described by Kato et al., supra. The two strains differ by up to 30% in regions of putative nonstructural genes, but show greater than 98% homology in the 5' untranslated region and 92% homology in the 5' portion of the capsid or core gene.

The isolate of the present invention, termed here C9, is more distantly related to both strains. This new isolate, is

TABLE 1

| Oligo | Sequence Listing | Sequence | Position (nt) |
|---|---|---|---|
| KY65 | SEQ ID NO: 1 | 5'-CCAAGCTT CACCAT AGAT CACT | 16–29 |
| KY79 | SEQ ID NO: 2 | 5'-GGCGACACT CCACCAT AGAT CACT | 6–29 |
| KY98 | SEQ ID NO: 3 | 5'-CCAAGCTT AGAT CACT CCCCT GT GAGGAACT | 21–44 |
| KY96 | SEQ ID NO: 4 | 5'-CCAAGCTT CACGCAGAAAGCGT CT AGCCAT | 50–74 |
| KY80 | SEQ ID NO: 5 | 5'-GCAGAAAGCGT CT AGCCAT GGCGT | 56–79 |
| KY144 | SEQ ID NO: 6 | 5'-ACGCAGAAAGCGT CT AGCCAT GGCGT | 54–79 |
| KY83 | SEQ ID NO: 7 | 5'-CCT CCAGGACCCCCCCT CCCGGGAGAGCCA | 99–128 |
| KY84 | SEQ ID NO: 8 | 5'-GAGT ACACCGGAATT GCCAGGACGACC | 149–175 |
| KY85 | SEQ ID NO: 9 | 5'-ACCCGCT CAAT GCCT GGAGAT | 194–214 |
| KY67 | SEQ ID NO: 10 | 5'-CGAAGCTT GCT AGCCGAGT AGT | 236–250 |
| KY81 | SEQ ID NO: 11 | 5'-CCGCAAGACT GCT AGCCGAGT AGT | 227–250 |
| KY88 | SEQ ID NO: 12 | 5'-GTT GGGT CGCGAAAGGCCTT GT GGT | 251–275 |
| KY86 | SEQ ID NO: 13 | 5'-GGT GCTT GCGAGT GCCCCGGGAGGT CT CGT | 288–317 |
| KY87 | SEQ ID NO: 14 | 5'-GACTT CCGAGCGGT CGCAACCT CG | 482–505 |

Table 2 lists oligonucleotides that function as negative sense (downstream) primers or as probes. The same internal ordering as in Table 1 is used.

93% similar to the consensus 5' untranslated region. It has only about 85% homology in the 5' portion of the core gene

TABLE 2

| Oligo | Sequence Listing | Sequence | Position (nt) |
|---|---|---|---|
| KY153 | SEQ ID NO: 15 | 5'-CCCAACACT ACT CGGCT AGCAGT CT | 232–256 |
| KY149 | SEQ ID NO: 16 | 5'-AAGGCCTTT CGCGACCCAACACT ACT | 245–278 |
| KY148 | SEQ ID NO: 17 | 5'-CACAAGGCCTTT CGCGACCCAACACT | 248–273 |
| KY78 | SEQ ID NO: 18 | 5'-CT CGCAAGCACCCT AT CAGGCAGT | 276–299 |
| KY145 | SEQ ID NO: 19 | 5'-CACT CGCAAGCACCCT AT CAGGCAGT | 276–301 |
| KY95 | SEQ ID NO: 20 | 5'-GGGAATT CGCAAGCACCCT AT CAGGCAGT | 276–298 |
| KY100 | SEQ ID NO: 21 | 5'-CGAGGTT GCGACCGCT CGGAAGT | 483–505 |
| KY110 | SEQ ID NO: 22 | 5'-AGGTT GCGACCGCT CGGAAGT | 483–503 |
| KY112 | SEQ ID NO: 23 | 5'-AGGTT GCGACCGCT CGGAAGT | 483–503 |
| KY109 | SEQ ID NO: 24 | 5'-AAT GCCAT AGAGGGGCCAAGG | 573–593 |
| KY111 | SEQ ID NO: 25 | 5'-ATT GCCAT AGAGGGGCCAAGG | 573–594 |
| KY99 | SEQ ID NO: 26 | 5'-CAGAATT CATT GCCAT AGAGGGGCCAAGGAT | 570–592 |
| KY68 | SEQ ID NO: 27 | 5'-CAGAATT CGCCCT CATT GCCAT | 586–599 |
| KY82 | SEQ ID NO: 28 | 5'-CCCACCCCAAGCCCT CATT GCCAT | 586–610 |

Several of the oligonucleotides have hybridizing regions modified to include a restriction site toward the 5'-end of the molecule. The restriction site is introduced into the amplified region with either the prototype or the Japanese strain (see, Table 3, below).

Figure 1B:
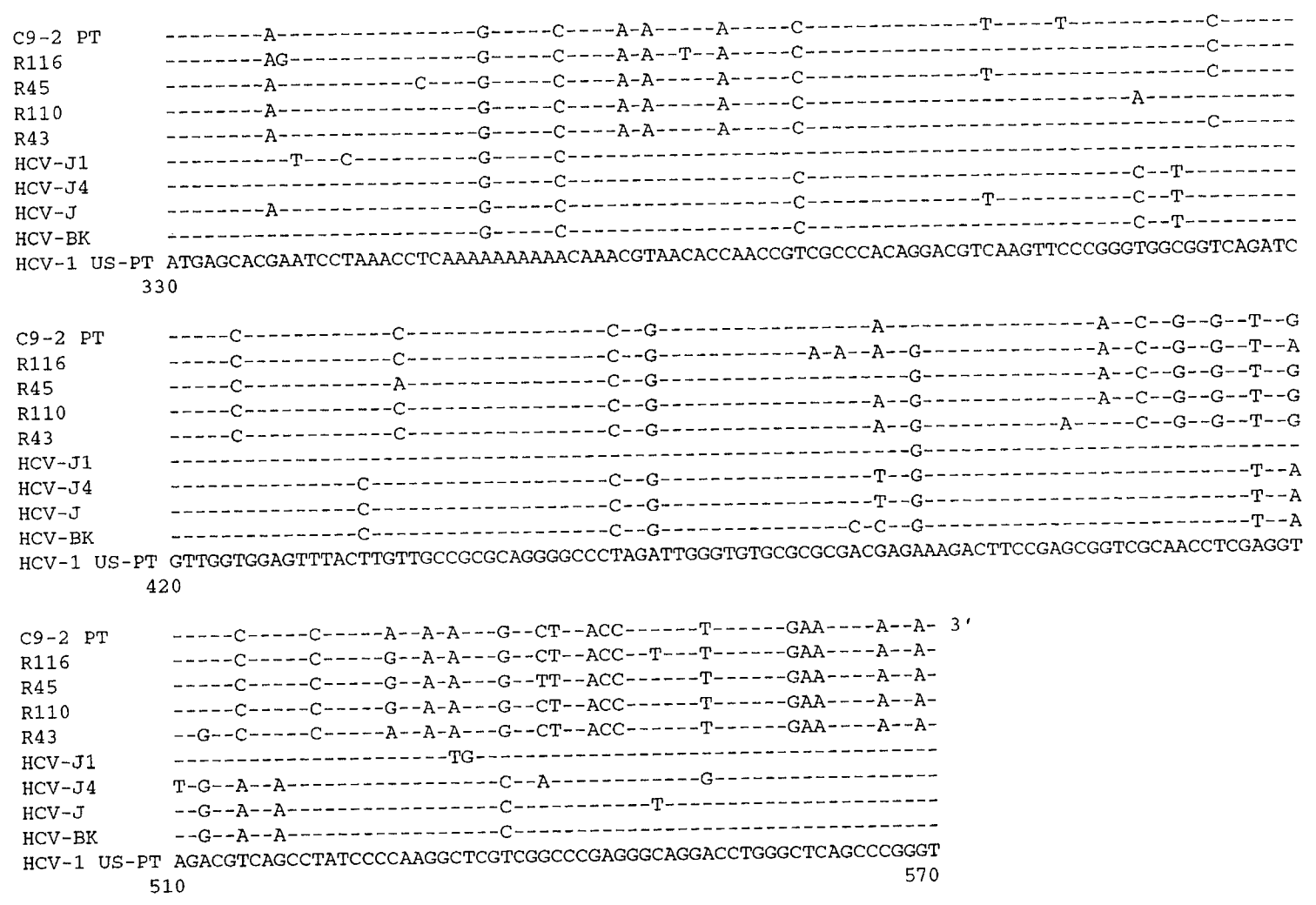

The C9 (SEQ ID NO. 29) variant and related isotypes, R45 (SEQ ID No. 31 ), R43 (SEQ ID NO. 33), R110 (SEQ ID NO. 32), and R116 (SEQ ID NO. 30) (see FIG. 1), were cloned into the RI/HindIII restriction sites in pBS(+) purchased from Stratagene as described above. The variant viruses were cloned using purified viral DNA targets and PCR cloning methods as described in U.S. Pat. No. 4,800,159, incorporated herein by reference. The resulting plasmids were transformed into *E. coli* strain DG101 (ATCC Deposit No. 47043).

Nucleotide sequences from the 5' untranslated sequence and the 5'-end of the capsid gene of the prototype C9 isolate and four related isolates are disclosed in C9 (SEQ ID NO. 29), R116 (SEQ ID NO. 30), R45 (SEQ ID No. 31), R110 (SEQ ID NO. 32), and R43 (SEQ ID. NO. 33) and show below. The sequences shown do not include primers KY96 (SEQ ID NO. 4) and KY99 (SEQ ID NO. 26), which were used to facilitate cloning the viral sequences.

C9 - SEQ ID NO. 29

| | | | | | |
|---|---|---|---|---|---|
| 1 | ACTGTCTTCA | CGCAGAAAGC | GTCTAGCCAT | GGCGTTAGTA | TGAGTGTCGT |
| 51 | ACAGCCTCCA | GGCCCCCCCC | TCCCGGGAGA | GCCATAGTGG | TCTGCGGAAC |
| 101 | CGGTGAGTAC | ACCGGAATTA | CCGGAAAGAC | TGGGTCCTTT | CTTGGATAAA |
| 151 | CCCACTCTGT | GTCCGGTCAT | TTGGGCGTGC | CCCCGCAAGA | CTGCTAGCCG |
| 201 | AGTAGCGTTG | GGTTGCGAAA | GGCCTTGTGG | TACTGCCTGA | TAGGGTGCTT |
| 251 | GCGAGTGCCC | CGGGAGGTCT | CGTAGACCGT | GCATCATGAG | CACAAATCCT |
| 301 | AAACCTCAAA | GAAAAACCAA | AAGAAACACA | AACCGCCGCC | CACAGGACGT |
| 351 | TAAGTTTCCG | GGTGGCGGCC | AGATCGTTGG | CGGAGTTTAC | TTGCTGCCGC |
| 401 | GCAGGGGCCC | CAGGTTGGGT | GTGCGCGCGA | CAAGAAAGAC | TTCCGAGCGA |
| 451 | TCCCAGCCGC | GTGGGAGACG | CCAGCCCATC | CCAAAAGATC | GGCGCTCCAC |
| 501 | CGGCAAGTCC | TGGGGAAAGC | CAGGAT | | |

R116 - SEQ ID NO. 30

| | | | | | |
|---|---|---|---|---|---|
| 1 | GGCGTTAGTA | TGAGTGTCGT | ACAGCCTCCA | GGCCCCCCCC | TCCCGGGAGA |
| 51 | GCCATAGTGG | TCTGCGGAAC | CGGTGAGTAC | GCCGAATTAC | CGGAAAGACT |
| 101 | GGGTCCTTTC | TTGGATAAAC | CCACTCTATG | TCCGGTCATT | TGGGCGTCCC |
| 151 | CCGCAAGACT | GCTAGCCGAG | TAGCGTTGGG | TTGCGAAAGG | CCTTGTGGTA |
| 201 | CTGCCTGATA | GGGTGCTTGC | GAGTGCCCCG | GGAGGTCTCG | TAGACCGTGC |
| 251 | ATCATGAGCA | CAGATCCTAA | ACCTCAAAGA | AAAACCAAAA | GAAATACAAA |
| 301 | CCGCCGCCCA | CAGGACGTCA | AGTTCCCGGG | TGGCGGCCAG | ATCGTTGGCG |
| 351 | GAGTTTACTT | GCTGCCGCGC | AGGGGCCCCA | GGTTGGGTGT | GCGCACAACA |
| 401 | AGGAAGACTT | CCGAGCGATC | CCAGCCGCGT | GGAAGACGCC | AGCCCATCCC |
| 451 | GAAAGATCGG | CGCTCCACCG | GTAAGTCCTG | GGGAAAGCCA | GGAT |

R45 - SEQ ID NO. 31

| | | | | | |
|---|---|---|---|---|---|
| 1 | GGCGTTAGTA | TGAGTGTCGT | ACAGCCTCCA | GGCCCCCCCC | TCCCGGGAGA |
| 51 | GCCATAGTGG | TCTGCGGAAC | CGGTGAGTAC | GCCGAATTGC | CGGAAAGACT |
| 101 | GGGTCCTTTC | TTGGATAAAC | CCACTCTATG | TCCGGTCATT | TGGGCGTCCC |
| 151 | CCGCAAGACT | GCTAGCCGAG | TAGCGTTGGG | TTGCGAAAGG | CCTTGTGGTA |
| 201 | CTGCCTGATA | GGGTGCTTGC | GAGTGCCCAG | GGAGGTCTCG | TAGACCGTGC |
| 251 | ATCATGAGCA | CAAATCCTAA | ACCCCAAAGA | AAAACCAAAA | GAAACACAAA |
| 301 | CCGCCGCCCA | CAGGACGTTA | AGTTCCCGGG | TGGCGGCCAG | ATCGTTGGCG |
| 351 | GAGTTTACTT | GATGCCGCGC | AGGGGCCCCA | GGTTGGGTGT | GCGCGCGACG |
| 401 | AGGAAGACTT | CCGAGCGATC | CCAGCCGCGT | GGGAGACGCC | AGCCCATCCC |
| 451 | GAAAGATCGG | CGTTCCACCG | GCAAGTCCTG | GGGAAAGCCA | GGAT |

R110 - SEQ ID NO. 32

| | | | | | |
|---|---|---|---|---|---|
| 1 | GGCGTTAGTA | TGAGTGTCGT | ACAGCCTCCA | GGCCCCCCCC | TCCCGGGAGA |
| 51 | GCCATAGTGG | TCTGCGGAAC | CGGTGAGTAC | GCCGAATTGC | CGGAAAGACT |
| 101 | GGGTCCTTTC | TTGGATTAAC | CCACTCTATG | TCCGGTCATT | TGGGCGTCCC |
| 151 | CCGCAAGACT | GCTAGCCTAG | TAGCGTTGGG | TTGCGAACGG | CCTTGTGGTA |
| 201 | CTGCCTGATA | GGGTGCTTGC | GAGTGCCCCG | GGAGGTCTCG | TAGACCGTGC |
| 251 | ATCATGAGCA | CAAATCCTAA | ACCTCAAAGA | AAAACCAAAA | GAAACACAAA |
| 301 | CCGCCGCCCA | CAGGACGTCA | AGTTCCCGGG | AGGCGGTCAG | ATCGTTGGCG |
| 351 | GAGTTTACTT | GCTGCCGCGC | AGGGGCCCCA | GGTTGGGTGT | GCGCGCGACA |
| 401 | AGGAAGACTT | CCGAGCGATC | CCAGCCGCGT | GGGAGACGCC | AGCCCATCCC |
| 451 | GAAAGATCGG | CGCTCCACCG | GCAAGTCCTG | GGGAAAGCCA | GGAT |

R43 - SEQ ID NO. 33

| | | | | | |
|---|---|---|---|---|---|
| 1 | GGCGTTAGTA | TGAGTGTCGT | ACAGCCTCCA | GGCCCCCCCC | TCCCGGGAGA |
| 51 | GCCATAGTGG | TCTGCGGAAC | CGGTGAGTAC | ACCGAATTAC | CGGAAAGACT |
| 101 | GGGTCCTTTC | TTGGATAAAC | CCACTCTATG | TCCGGTCATT | TGGGCGTCCC |
| 151 | CCGCAAGACT | GCTAGCCTAG | TAGCGTTGGG | TTGCGAACGG | CCTTGTGGTA |
| 201 | CTGCCTGATA | GGGTGCTTGC | GAGTGCCCCG | GGAGGTCTCG | TAGACCGTGC |
| 251 | ATCATGAGCA | CAAATCCTAA | ACCTCAAAGA | AAAACCAAAA | GAAACACAAA |
| 301 | CCGCCGCCCA | CAGGACGTCA | AGTTCCCGGG | TGGCGGCCAG | ATCGTTGGCG |
| 351 | GAGTTTACTT | GCTGCCGCGC | AGGGGCCCCA | GGTTGGGTGT | GCGCGCGACA |
| 401 | AGGAAGACTT | CCGAACGGTC | CCAGCCGCGT | GGGAGGCGCC | AGCCCATCCC |
| 451 | AAAAGATCGG | CGCTCCACCG | GCAAGTCCTG | GGGAAAGCCA | GGAT |

Clones containing the vital sequences have been deposited with the American Type Culture Collection, Baltimore, Maryland as follows:

| Isolate | SEQ ID NO. | Plasmid Designation | ATCC Deposit No. | Date of Deposit |
|---------|------------|---------------------|------------------|-----------------|
| C9 | 29 | pHCV-C9 | 75265 | July 2, 1992 |
| R110 | 32 | pHCV-R110 | 75266 | July 2, 1992 |

Plasmid pHCV-C9 contains the novel variant C9 sequence. The alignment of the four related variants with the C9 sequences is shown in FIG. 1. The source of the sequence data for known isolates was as follows: HCV-J 1, HCV-J4 (Okamoto et al., 1990, *Japan J. Exp. Med.* 6(3):167–177); HCV-J (Kato et al., 1990, *Mol. Biol. Med.* 7:495–501); HCV-BK (Takamizawa et al., 1991, *J. Virol.* 65:1105–1113); and HCV-1 US-PT (Hah et al., 1991, *Proc. Natl. Acad. Sci. USA* 88:1711–1715) The numbering is according to Karo et al., 1990, *Proc. Natl. Acad. Sci. USA* 87:9524–9528.

TABLE 3

Determination of nucleotide and amino acid sequence homology of C9 isolate to prototype U.S. (PT-HCV) and Japanese isolates (J-HCV).

| Sequences | Isolate | PT-HCV | J-HCV |
|-----------|---------|--------|-------|
| 5'-UTR nucleotide (255) | C9 | 92.9% | 92.9% |
| | J-HCV | 98.8% | — |
| Core nucleotide (244) | C9 | 84.3% | 85.1% |
| | J-HCV | 92.1% | — |
| amino acid (80) | C9 | 91.3% | 90.0% |
| | J-HCV | 98.7% | — |

Thus, the present invention provides materials and methods for assays that are specific to the C9 isolate and distinguish the isolate from other hepatitis isolates. In some embodiments the methods of the invention are based on nucleic acid hybridization with or without the use of PCR to amplify the targeted sequences. In other embodiments, the methods use immunoglobulins specific to the C9 isolate. The oligonucleotide sequences of primers and probes specific to C9 are presented in Table 4, below.

TABLE 4

| | Probes | |
|---|---|---|
| SEQ ID NO. 37 | MY160 5'-TGTCCGGTCATTTGGGCG-3' | (nt216–233) |
| SEQ ID NO. 34 | (1) 5'-TTGCCGGAAAGACTGGGTCCTTTC-3' | (nt174–197) |
| SEQ ID NO. 35 | (2) 5'-CAAAAGAAACACAAACCGCCGCCC-3' | (nt374–397) |
| SEQ ID NO. 36 | (3) 5'-CCAGCCCATCCCGAAAGATCGGCG-3' | (nt527–550) |
| | Upstream Primers | |
| SEQ ID NO. 38 | (1) 5'-AAACCCACTCTATGTCCGGTC-3' | (nt204–224) |
| SEQ ID NO. 39 | (2) 5'-GTACGCCGGAATTGCCGGAAA-3' | (nt163–183) |
| SEQ ID NO. 40 | (3) 5'-CCTCAAAGAAAAACCAAAAGA-3' | (nt360–380) |
| | Downstream Primers | |
| SEQ ID NO. 41 | (4) 5'-TGGCGTCTCCCACGCGGCTGG-3' | (nt509–529) |
| SEQ ID NO. 42 | (5) 5'-CTTTCCCCAGGACCTGCCGGT-3' | (nt555–575) |

The numbering system used to identify the nucleotides is from Kato et al., 1990, *Proc. Natl. Acad. Sci., supra*.

One oligonucleotide, KY150, is useful for the detection of both the C9 isolate and the previously known HCV protype isolates. This oligonucleotide has the following sequence:

5'-CATAGTGGTCTGCGGAACCGGTGAGT-3'    (SEQ ID NO. 43).

It will be apparent to one of skill in the art that any upstream/downstream primer pair shown in Table 4 is suitable for specifically amplifying the C9 isolate and related isotypes. It will be additionally apparent to select a C9-specific probe suitable for hybridizing the amplified nucleic acid subsequence using as guidance the nucleotide positions provided in Table 4.

In a preferred embodiment, the primers of the invention are used in conjunction with a polymerase chain reaction (PCR) amplification of the target nucleic acid. Because HCV is an RNA virus, the first step in the amplification is the synthesis of a DNA copy (cDNA) of the region to be amplified. Reverse transcription can be carried out as a separate step, or, as described below, in a homogeneous reverse transcription polymerase chain reaction (RT-PCR), a modification of the polymerase chain reaction for amplifying RNA.

Although the PCR process is well known in the art (see U.S. Pat. Nos. 4,683,195; 4,683,202; and 4,965,188, each of which is incorporated herein by reference) and although commercial vendors, such as Perkin Elmer, sell PCR reagents manufactured and developed by Hoffmann-La Roche and publish PCR protocols, some general PCR information is provided below for purposes of clarity and full understanding of the invention for those unfamiliar with the PCR process.

To amplify a target nucleic acid sequence in a sample by PCR, the sequence must be accessible to the components of the amplification system. In general, this accessibility is ensured by isolating the nucleic acids from the sample. A variety of techniques for extracting ribonucleic acids from biological samples are known in the art. For example, see those described in Rotbart et al., 1989, in *PCR Technology* (Erlich ed., Stockton Press, New York) and Han et al. 1987, *Biochemistry* 26:1617–1625. Alternatively, if the sample is fairly readily disruptable, the nucleic acid need not be purified prior to amplification by the PCR technique, i.e., if the sample is comprised of cells, particularly peripheral blood lymphocytes or monocytes, lysis and dispersion of the intracellular components may be accomplished merely by suspending the cells in hypotonic buffer.

The first step of each cycle of the PCR involves the separation of the nucleic acid duplex. Of course, if the target nucleic acid is single- stranded, i.e., single-stranded RNA, no initial separation step is required during the first cycle. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In the preferred embodiment of the PCR process, strand separation is achieved by heating the reaction to a sufficiently high temperature for an sufficient time to cause the denaturation of the duplex but not to cause an irreversible denaturation of the polymerase (see U.S. Pat. No. 4,965, 188). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology* 43:63–67; and Radding, 1982, *Ann. Rev. Genetics* 16:405–436).

Template-dependent extension of primers in PCR is catalyzed by a polymerizing agent in the presence of adequate amounts of four deoxyribonucleoside triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis. Because Hepatitis C is an RNA virus, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer. Typically, the genomic RNA/cDNA duplex template is heat denatured during the first denaturation step after the initial reverse transcription step leaving the DNA strand available as an amplification template. Suitable polymerases for use with a DNA template include, for example, *E. coli* DNA polymerase I or its Klenow fragment, $T_4$ DNA polymerase, Tth polymerase, and Taq polymerase, a heat-stable DNA polymerase isolated from *Thermus aquaticus* and developed and manufactured by Hoffmann-La Roche and commercially available from Perkin Elmer. The latter enzyme is widely used in the amplification and sequencing of nucleic acids. The reaction conditions for using Taq polymerase are known in the art and are described in Gelfand, 1989, *PCR Technology*, supra.

When RNA is amplified, an initial reverse transcription (RT) step is carried out to create a DNA copy (cDNA) of the RNA. PCT patent publication No. WO 91/09944, published Jul. 11, 1991, incorporated herein by reference, describes high-temperature reverse transcription by a thermostable polymerase that also functions in PCR amplification. High-temperature RT provides greater primer specificity and improved efficiency. Copending U.S. patent application Serial No. 07/746, 121, filed Aug. 15, 1991, incorporated herein by reference, describes a "homogeneous RTPCR" in which the same primers and polymerase suffice for both the reverse transcription and the PCR amplification steps, and the reaction conditions are optimized so that both reactions occur without a change of reagents. *Thermus thermophilus* DNA polymerase, a thermostable DNA polymerase that can function as a reverse transcriptase, is used for all primer extension steps, regardless of template. Both processes can be done without having to open the tube to change or add reagents; only the temperature profile is adjusted between the first cycle (RNA template) and the rest of the amplification cycles (DNA template).

The 5' terminal end of the HCV genome is predicted to have significant secondary structure that could hinder reverse transcription with a reverse transcriptase such as Moloney murine leukemia virus RT by interfering with primer hybridization. Unfortunately, raising the reaction temperature to denature the secondary structure also inactivates most reverse transcriptase enzymes. The use of the reverse transcriptase activity of recombinant *Thermus thermophilus* (rTth) DNA polymerase allows the cDNA synthesis to take place at elevated temperatures without enzyme inactivation. The primers of the present invention remain hybridized to the RNA template at this elevated reverse transcription temperature.

The PCR method can be performed in a step-wise fashion, where after each step new reagents are added, or in a fashion where all of the reagents are added simultaneously, or in a partial step-wise fashion, where fresh or different reagents are added after a given number of steps. For example, if strand separation is induced by heat, and the polymerase is heat-sensitive, then the polymerase has to be added after every round of strand separation. However, if, for example, a helicase is used for denaturation, or if a thermostable polymerase is used for extension, then all of the reagents may be added initially, or, alternatively, if molar ratios of reagents are of consequence to the reaction, the reagents may be replenished periodically as they are depleted by the synthetic reaction.

Those skilled in the art will know that the PCR process is most usually carried out as an automated process with a thermostable enzyme. In this process, the temperature of the reaction mixture is cycled through a denaturing region, a primer annealing region, and an extension reaction region. Alternatively, the annealing and extension temperature can be the same. The RT-PCR described in the examples uses such a two-step temperature cycling. A machine specifically adapted for use with a thermostable enzyme is commercially available from Perkin Elmer.

Those skilled in the art will also be aware of the problems of contamination of a PCR by the amplified nucleic acid from previous reactions and nonspecific amplification. Methods to reduce these problems are provided in PCT patent application Ser. No. 91/05210, filed Jul. 23, 1991, incorporated herein by reference. The method allows the enzymatic degradation of any amplified DNA from previous reactions and reduces nonspecific amplification. The PCR amplification is carried out in the presence of dUTP instead of dTTP. The resulting double-stranded, uracil-containing product is subject to degradation by uracil N-glycosylase (UNG), whereas normal thymine-containing DNA is not degraded by UNG. Adding UNG to the amplification reaction mixture before the amplification is started degrades all uracil-containing DNA that might serve as target. Because the only source of uracil-containing DNA is the amplified product of a previous reaction, this method effectively sterilizes the reaction mixture, eliminating the problem of contamination from previous reactions (carry-over). UNG itself is rendered temporarily inactive by heat, so the denaturation steps in the amplification procedure also serve to inactivate the UNG. New amplification products, therefore, though incorporating uracil, are formed in an effectively UNG-free environment and are not degraded.

A preferred embodiment of the invention utilizes a homogeneous RT/PCR method which incorporates a sterilization step. This one tube, non-addition reaction serves to sterilize the RT-PCR reaction preventing carryover contamination and providing amplified detectable PCR product from a sample containing an RNA target. This method is exemplified in Example 6.

Those practicing the present invention should note that, although the preferred embodiment incorporates RT-PCR amplification, amplification of target sequences in a sample may be accomplished by any known method, such as ligase chain reaction (LCR), transcription amplification, and self-sustained sequence replication, each of which provides sufficient amplification so that the target sequence can be detected by nucleic acid hybridization to an SSO probe. Alternatively, methods that amplify the probe to detectable levels can be used, such as Qβ-replicase amplification. The term "probe" encompasses the sequence specific oligonucleotides used in the above procedures; for instance, the two or more oligonucleotides used in LCR are "probes" for purposes of the present invention, even though some embodiments of LCR only require ligation of the probes to indicate the presence of an allele.

Sequence-specific probe hybridization is an important step in the successful performance of the present methods. The sequence specific oligonucleotide probes of the present invention hybridize specifically with a particular segment of the HCV genome and have destabilizing mismatches with the sequences from other organisms. Under sufficiently stringent hybridization conditions, the probes hybridize specifically only to exactly complementary sequences. The stringency of the hybridization conditions can be relaxed to tolerate varying amounts of sequence mismatch. Detection of the amplified product utilizes this sequence-specific hybridization to insure detection of only the correct amplified target, thereby decreasing the chance of a false positive caused by the presence of homologous sequences from related organisms.

The assay methods for detecting hybrids formed between SSO probes and nucleic acid sequences can require that the probes contain additional features in addition to the hybridizing region. For example, if the probe is first immobilized, as in the "reverse" dot blot format described below, the probe can also contain long stretches of poly-dT that can be fixed to a nylon support by irradiation, a technique described in more detail in PCT Patent Publication No. 89/11548, incorporated herein by reference. In the dot blot format, immobilized target is hybridized with probes containing a compound used in the detection process, as discussed below.

The probes of the invention can be synthesized and labeled using the techniques described above for synthesizing oligonucleotides. The probe can be labeled at the 5'-end with $^{32}$P by incubating the probe with $^{32}$P-ATP and kinase. A suitable nonradioactive label for SSO probes is horseradish peroxidase (HRP). Methods for preparing and detecting probes containing this label are described in the Examples below and in U.S. Pat. Nos. 4,914,210 and 4,962,029; the latter patents are incorporated herein by reference. For additional information on the use of such labeled probes, see U.S. Pat. No. 4,789,630; Saiki et al, 1988, *N. Eng. J. Med.* 319:537–541; and Bugawan et al., 1988, *Bio/Technology* 6:943–947, each of which is incorporated herein by reference. Useful chromogens include red leuco dye and 3,3',5, 5'-tetramethylbenzidine (TMB).

The probes of the invention can be used to determine if viral sequences are present in a sample by determining if the SSO probes bind to the viral sequences present in the sample. Suitable assay methods for purposes of the present invention to detect hybrids formed between SSO probes and nucleic acid sequences in a sample are known in the art. For example, the detection can be accomplished using a dot blot format, as described in the Examples. In the dot blot format, the unlabeled amplified sample is bound to a solid support, such as a membrane, the membrane incubated with labeled probe under suitable hybridization conditions, the unhybridized probe removed by washing, and the filter monitored for the presence of bound probe. When multiple samples are analyzed with a single probe, the dot blot format is quite useful. Many samples can be immobilized at discrete locations on a single membrane and hybridized simultaneously by immersing the membrane in a solution of probe.

An alternate method that is quite useful when large numbers of different probes are to be used is a "reverse" dot blot format, in which the amplified sequence contains a label, and the probe is bound to the solid support. This format would be useful if the test of the present invention were used as one of a battery of tests to be performed simultaneously. In this format, the unlabeled SSO probes are bound to the membrane and exposed to the labeled sample under appropriately stringent hybridization conditions. Unhybridized labeled sample is then removed by washing under suitably stringent conditions, and the filter is then monitored for the presence of bound sequences.

Both the forward and reverse dot blot assays can be carried out conveniently in a microtiter plate; see U.S. Ser. No. 695,072, filed May 3, 1991, which is a CIP of U.S. Ser. No. 414,542, filed Sept. 29, 1989, now abandoned, incorporated herein by reference. The probes can be attached to bovine serum albumen (BSA), for example, which adheres to the microliter plate, thereby immobilizing the probe.

Another suitable assay system is described in U.S. patent application Ser. No. 563,758, filed Aug. 6, 1990, incorporated herein by reference, in which a labeled probe is added during the PCR amplification process. Any SSO probe that hybridizes to target DNA during each synthesis step is degraded by the 5' to 3' exonuclease activity of a polymerase, e.g., Taq polymerase. The degradation product from the probe is then detected. Thus, the presence of the breakdown product indicates that the hybridization between the SSO probe and the target DNA occurred.

The nucleotide sequences provided above are an important aspect of the present invention. Although only one strand of the sequence is shown, those of skill in the art recognize that the other strand of the sequence can be inferred from the information depicted above. This information enables the construction of other probes and primers of the invention.

The present invention also relates to kits, multicontainer units comprising useful components for practicing the present method. A useful kit can contain SSO probes for detecting Hepatitis C virus nucleic acid. In some cases, the SSO probes may be fixed to an appropriate support membrane. The kit can also contain primers for RT-PCR, as such primers are useful in the preferred embodiment of the invention. Other optional components of the kit include, for example, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. In addition to the above components, the kit can also contain instructions for carrying out the present method.

In addition to the use of PCR and nucleic acid probes, the present invention also provides methods for raising immunoglobulins specific for particular HCV isolates. This is typically accomplished by first expressing vital nucleotide sequences and then using the expressed proteins to raise antibodies specific to the desired isolate.

The nucleotide sequences of the hepatitis isolates can be used in a variety of recombinant expression systems. In this manner, desired genes, such as the capsid gene, can be expressed. Recombinant expression of nucleotide sequences in prokaryotic or eukaryotic hosts is well known in the art (see Sambrook et al., supra.). The expressed proteins can be used to raise immunoglobulins specific to the isolate. The immunoglobulins can then be used in assays to detect the presence of the virus, as described below. The proteins can also be used to detect the presence of antibodies in patients exposed to the virus.

The desired viral sequences are conveniently inserted into a suitable vector before transformation using standard techniques into mammalian, yeast or insect cell lines for expression. Prokaryotes are preferably used for intermediate cloning steps.

The particular procedure used to introduce the altered genetic material into the host cell for expression of the viral sequences is not particularly critical. Any of the well known procedures for introducing foreign nucleotide sequences into host cells may be used. These include the use of calcium phosphate transfection, polybrene, protoplast fusion, electroporation, liposomes, microinjection, plasmid vectors, viral vectors and any of the other well known methods for introducing cloned genomic DNA, cDNA, synthetic DNA or other foreign genetic material into a host cell (see Sambrook et al., supra). It is only necessary that the particular genetic engineering procedure utilized be capable of successfully introducing into the host cell at least one gene that is capable of expressing the desired viral protein.

The particular vector used to transport the genetic information into the cell is also not particularly critical. Any of the conventional vectors used for expression of recombinant proteins in eukaryotic cells may be used.

The expression vector contains a eukaryotic transcription unit or expression cassette that contains all the elements required for the expression of the vital nucleic acid sequences in eukaryotic cells. A typical expression cassette contains a promoter operably linked to the DNA sequence encoding a vital protein and signals required for efficient polyadenylation of the transcript.

The vectors usually comprise selectable markers such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, DHFR, and asparagine synthetase and ouabain selection.

The expression vector of the present invention will typically contain both prokaryotic sequences that facilitate the cloning of the vector in bacteria as well as one or more eukaryotic transcription units that are expressed only in eukaryotic cells, such as mammalian cells. The vector may or may not comprise a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the transfected DNA integrates into the genome of the transfected cell, where the promoter directs expression of the desired gene. The expression vector is typically constructed from elements derived from different, well-characterized vital or mammalian genes. For a general discussion of the expression of cloned genes in cultured mammalian cells, see Sambrook et al., supra, Ch. 16.

After the expression vector is introduced into the cells, the transfected cells are cultured under conditions favoring expression of the viral protein and the protein is recovered from the culture using standard techniques. A number of standard procedures for purifying proteins can be used, such as, for example, ammonium sulfate precipitation, gel electrophoresis, ion exchange chromatography, size exclusion chromatography or affinity chromatography. See, generally, Scopes, R., *Protein Purification,* Springer-Verlag, N.Y. (1982).

In addition to the use of proteins encoded by the desired viral genome, peptides that mimic epitopes specific to the virus can also be used to raise antibodies specific to the virus. Such technology is well known to those of skill in the art and is described, for instance, in Geysen et al., *Multipin Peptide Synthesis - A Review,* Coselco Mimotypes, PTY Ltd., which is incorporated herein by reference.

The polypeptides discussed above are then used to raise antibodies using standard procedures. The immunoglobulins may be used for a variety of applications. For instance, they can be used to assay for the presence of the virus in a biological sample or to purify the vital antigens, for example, using affinity chromatography. They may also be used to neutralize the corresponding protein, including inhibition of infectiousness of the entire virus. The multitude of techniques available to those skilled in the art for production and manipulation of various immnunoglobulin molecules can thus be readily applied to produce molecules useful for diagnosis and detection of the particular isolate.

As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. Immunoglobulins may exist in a variety of forms besides antibodies, including for example, Fv, Fab, and $F(ab)_2$, as well as in single chains (e.g., Huston et al., 1988, *Proc. Natl. Acad. Sci. USA* 85:5879–5883; Bird et al., 1988, *Science* 242:423–426; and Hunkapiller and Hood, 1986, *Nature* 323:15–16, which are incorporated herein by reference). For a general review of immunoglobulin structure and function see, *Fundamental Immunology,* 2d Ed., W.E. Paul ed., Ravens Press, N.Y., (1989).

Antibodies that bind epitopes specific to the desired isolate may be produced by a variety of means. The production of nonhuman monoclonal antibodies, e.g., murine, lagomorpha, equine, etc., is well known and may be accomplished by, for example, immunizing the animal with a preparation containing the virus or a fragment thereof. Antibody-producing cells obtained from the immunized animals are immortalized and screened using standard techniques. For a discussion of general procedures of monoclonal antibody production see Harlow and Lane, *Antibodies, A Laboratory Manual* Cold Spring Harbor Publications, N.Y. (1988), which is incorporated herein by reference.

In some circumstances, it may be desirable to transfer the antigen binding regions of the nonhuman antibodies, e.g., the F(ab')$_2$ or hypervariable regions, to human constant regions (Fc) or framework regions by recombinant DNA techniques to produce substantially human molecules. Such methods are generally known in the art and are described in, for example, U.S. Pat. No. 4,816,397, EP publications 173,494 and 239,400, which are incorporated herein by reference. Alternatively, one may isolate DNA sequences that encode a human monoclonal antibody or portions thereof that specifically bind to the virus by screening a DNA library from human B cells according to the general protocol outlined by Huse et al., 1986, *Science* 246:1275–1281, and then cloning and amplifying the sequences that encode the antibody (or binding fragment) of the desired specificity.

The immunoglobulins produced as described above can then be used in a variety of diagnostic assays for the presence of the hepatitis isolate. For instance, the labelled immunoglobulins specific for the C9 virus can be used in assays involving contacting the immunoglobulins with a sample suspected of containing the virus and detecting whether a complex is formed. The label may be coupled directly or indirectly to the immunoglobulin according to methods well known in the art. As discussed above in the context of labelled oligonucleotides, a wide variety of labels may be used. The component may be labeled by any one of several methods. A common method of detection is the use of autoradiography with $^3$H, $^{125}$I, $^{35}$S, $^{14}$C, or $^{32}$P labeled compounds or the like. The choice of radioactive isotope depends on research preferences due to ease of synthesis, varying stability, and half-lives of the selected isotopes. Nonradioactive labels include ligands that bind to labeled antibodies, fluorophores, chemiluminescent agents, and enzymes. The choice of label depends on sensitivity required, ease of conjugation with the compound, stability requirements and available instrumentation.

Nonradioactive labels are often attached by indirect means. Generally, a ligand molecule (e.g., biotin) is covalently bound to the molecule. The ligand then binds to an anti-ligand (e.g., streptavidin) molecule that is either inherently detectable or covalently bound to a signal system, such as a detectable enzyme, a fluorescent compound, or a chemiluminescent compound. Ligands and anti-ligands may be varied widely. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal-generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various signal-producing systems that may be used, see, U.S. Pat. No. 4,391,904, which is incorporated herein by reference.

To detect the presence of the complexes, the mixture will typically be contacted with a protein capable of binding the Fc region of the immunoglobulin, such as a second antibody, protein A, or protein G. The protein is preferably immobilized on a solid surface and the solid surface is washed to remove unbound immunoglobulins specific for the desired virus. Many methods for immobilizing biomolecules on solid surfaces are known in the art. For instance, the solid surface may be a membrane (e.g, nitrocellulose), a microtiter dish (e.g., PVC or polystyrene) or a bead. The desired component may be covalently bound or noncovalently attached through unspecific bonding. The label is then detected using standard techniques suitable for the particular label used.

The recombinantly expressed proteins discussed above or viral lysates may also be used in diagnostic procedures. These procedures typically involve contacting a biological sample (e.g. serum) suspected of containing antibodies to the virus and detecting the immunological reaction. The reaction is preferably detected using labelled proteins as described above. Suitable methods for such procedures are described in detail in U.S. Pat. No. 5,055,391, which is incorporated herein by reference.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Homogeneous RT-PCR Amplification

In the homogeneous RT-PCR, the same polymerase functions as both a reverse transcriptase and a DNA polymerase. This allows both the initial reverse transcription of the HCV genomic RNA and the subsequent amplification of the cDNA to be performed in the same tube without opening the tube in between steps to change reagents.

Nucleic acids were isolated from serum or plasma using the IsoQuick™ nucleic acid extraction kit from MicroProbe. All amplifications were done using a TC9600 Thermocycler™ and MicroAmp™ tubes, both from Perkin Elmer, in total reaction volumes of 20 µl. The reagents for each 20 µl reaction are listed in Table 5, below.

TABLE 5

| RT-PCR Reaction Mixture | |
|---|---|
| H$_2$O | 6.3 µl |
| 1OX RT Reaction Buffer (100 mM Tris-HCl (pH 8.3), 900 mM KCl) | 2.0 µl |
| MnCl$_2$ (10 mM, 0.85 mM final concentration) | 1.7 µl |
| dNTP (2 mM each of dATP, dCTP, dGTP, and dTTP in H$_2$O, pH 7.0) | 2.0 µl |
| Primer KY78 (SEQ ID NO. 18) (1.5 µM in H$_2$O, 3 picomole/reaction final concentration) | 2.0 µl |
| Primer KY 80 (SEQ ID NO. 5) (1.5 µM in H$_2$O, 3 picomole/reaction final concentration) | 2.0 µl |
| rTth DNA polymerase (Perkin Elmer, Norwalk, CT; 0.18 µM or 2.5 units/µl in 1X Enzyme storage buffer (20 µM Tris-HCl (pH 7.5), 100 mM KCl, 0.1 µM EDTA, 1 µM DTT, 0.2% Tween 20 (Pierce Surfactants), 50% glycerol [v/v]) | 2.0 µl |
| Template nucleic acid (<250 ng total in dH$_2$O) | 2.0 µl |

The TC9600 was programmed to provide the following reaction temperature profile. After preheating to 70° C. for 1 minute, the program was paused long enough to insert the reaction tubes, the program was restarted, and the reaction was held at 70° C. for 15 minutes to allow for reverse transcription. The reaction temperature was then raised to 95° C. for 1 minute to denature the RNA-cDNA duplex. Next, the reaction temperature underwent two cycles of 95° C. for 15 seconds and 60° C. for 20 seconds followed by 38 cycles of 90° C. for 15 seconds and 60° C. for 20 seconds. Finally, the reaction temperature was held at 60° C. for 4 minutes for the final extension step, cooled to 15° C., and held at that temperature until the analysis of the amplified sample could be performed.

EXAMPLE 2

Dot Blot Format

In this detection method, a small portion of the amplified DNA is denatured and applied to a nylon filter, which is then hybridized to a labeled probe. The probe hybridizing region is KY88 (SEQ ID NO. 12), and the probe is radioactivity labeled with $^{32}P$. Alternatively, the probe can be covalently conjugated to horseradish peroxidase (HRP) to provide a means of nonisotopic detection in the presence of a chromogenic or chemiluminescent substrate.

The amplification reaction is generally carried out as described in Example 1. The PCR-amplified product is then denatured by treatment with alkali. To 5 µl of PCR product is added 5 µl of 0.5 M EDTA, pH 8.0, 8 µl of 5 N NaOH, and 82 µl H$_2$O. The mixture is allowed to stand at room temperature for 10 minutes to complete the denaturation.

BioDyne™ B nylon filters (Pall Corp., Glen Cove, NY) are prepared by soaking in H$_2$O for 5 to 10 minutes and further rinsing with 200 µl of H$_2$O after the dot-blot manifold (Bio-Dot™ from Bio Rad, Richmond, Calif.) has been set up. After denaturation, 100 µl of the sample mixture is applied under vacuum to the nylon membrane using the dot blot apparatus. Each well is then rinsed with 200 µl of 0.4 N NaOH and the entire filter is rinsed briefly with 2X SSC, and air-dried until no pools of liquid are left. The DNA is immobilized and cross-linked to the nylon filter by ultraviolet irradiation at a flux of 1200 mJ/cm$^2$ with a Stratalinker™ (Stratagene, La Jolla, Calif.) UV light box (the "autocrosslink" setting).

Filters are "pre-hybridized" by soaking in the hybridization buffer (5X SSPE, 5X Denhardt's solution, 0.1% SDS, 50 µg/ml herring sperm DNA) in heat-sealable bags at 50° C. (air shaker) for at least 30 minutes. The buffer is then replaced with an equal amount of the same solution containing 1–2×10$^5$ cpm/m/probe, and the filter is allowed to hybridize between 2 hours and overnight at 50° C.

After hybridization, filters are washed three times in 2X SSPE/0.1% SDS; twice for 20 minutes at room temperature, and then once for twenty minutes at the high stringency temperature of 60° C. The filters are then blotter dry, wrapped in plastic wrap, and exposed to X-ray film at −70° C. with one or two intensifying screens.

An alternate method of visualization is to hybridize with horseradish peroxidase conjugated oligonucleotide probes, prepared as described by Levenson and Chang, 1989, in *PCR Protocols: A Guide to Methods and Applications* (Innis et all., eds., Academic Press, San Diego), pages 92–112, and Saiki et al., 1988, *N. Eng. J. Med.* 3 19:537–541, each of which is incorporated herein by reference. Hybridization is carried out with 2 pmoles of HRP-SSO probe per 5 ml of hybridization solution.

After washing, filters to be developed with a chromogenic dye substrate are rinsed in 100 mM sodium citrate, pH 5.0, then placed in 100 mM sodium citrate, pH 5.0, containing 0.1 mg/ml of 3,3',5,5'-tetramethylbenzidine per milliliter (Fluka) and 0.00 15 percent hydrogen peroxide, and incubated with gentle agitation for 10 to 30 minutes at room temperature. Developed filters are rinsed in water and immediately photographed. The TMB detection system is prepared and used substantially as described in the Ampli-Type™ DQα DNA typing kit marketed by Perkin Elmer. In another embodiment, filters are developed with the chemiluminescent detection system (ECL; Amersham, Arlington Heights, IL). Filters are rinsed in PBS for 5 minutes and placed in the ECL solution for 1 minute with gentle agitation. Filters are then exposed to X-ray film at room temperature for 1 to 5 minutes.

EXAMPLE 3

Reverse Dot Blot Format

In this embodiment of the invention, the probe hybridization region is KY88 (SEQ ID NO. 12), KY150 (SEQ ID NO. 43), or MY160 (SEQ ID NO.37), and the probe is fixed to a membrane. The amplified target DNA is hybridized to the membrane-bound probe as described in copending application Serial Nos. 197,000 and 347,495; Saiki et al., 1989, *Proc. Natl. Acad. Sci.* 86:6230–6234; and in the product insert of the AmpliType® DQalpha DNA typing kit marketed by Perkin Elmer, each of which is incorporated herein by reference. The amplification primers are biotinylated, as described in Levenson and Chang, 1989, *supra*, so that any amplified DNA that hybridizes to the membrane-bound probes can be easily detected.

In one embodiment, detection is carried out by reacting streptavidin conjugated horseradish peroxidase (SA-HRP) with any biotinylated, amplified DNA hybridized to the membrane-bound probe. The HRP thus becomes bound, through the SA-biotin interaction, to the amplified DNA and can be used to generate a signal by a variety of well-known means, such as the generation of a colored compound by the oxidation of tetramethylbenzidine (see U.S. Pat. No. 4,789, 630).

Although the probe can be fixed to the membrane by any means, a preferred method involves "tailing" the probe hybridizing region with a much longer sequence of poly-dT. The resulting poly-dT "tail" can then be reacted with amine groups on a nylon membrane to fix the probe covalently to the membrane. This reaction can be facilitated by UV irradiation.

Terminal deoxyribonucleotidyl transferase (TdT, Ratliff Biochemicals; for the reactions below assume a concentration of about 120 Units/µl, which is 100 pmole/µl) can be used to create a poly-dT tail on a probe, although one can also synthesize the tailed probe on a commercially available DNA synthesizer. When one uses a DNA synthesizer to make the tailed probe, however, one should place the tail on the 5'-end of the probe, so that undesired premature chain termination occurs primarily in the tail region.

TdT reactions should be carried out in a volume of about 100 µl containing 1X TdT salts, 200 pmole of oligonucleotide, 800 µM DTT, and 60 units of TdT. 10X TdT salts is 1,000 mM K-cacodylate, 10 mM COCl$_2$, 2 mM dithiothreitol, 250 mM Tris-Cl, pH 7.6, and is prepared as described by Roychoudhury and Wu, *Meth. Enzymol.* 65: 43–62, incorporated herein by reference. A 10X stock solution of 8 mM dTTP can be prepared (neutralized to pH 7 with NaOH) for convenience.

The TdT reaction should be carried out at 37° C. for two hours and then stopped by the addition of 100 μl of 10 mM EDTA, pH 8. The final concentration of tailed oligonucleotide is 1 μM (1 pmole/μl), and the length of the homopolymer tail is about 400 residues. Tail length can be changed by adjusting the molar ratio of dTTP to oligonucleotide. The tailed probes can be stored at −20° C. until use.

The nylon membrane preferred for the reverse dot blot format is the Biodyne™ B nylon membrane, 0.45 micron pore size, manufactured by Pall and also marketed by ICN as the BioTrans™ nylon membrane. The probes can be spotted onto the membrane very conveniently with the Bio-Dot™ dot blot apparatus manufactured by BioRad. Each probe is spotted onto a unique, discrete location on the membrane. About 2 to 10 picomoles of each tailed probe is premixed with 50 to 100 μl of TE buffer before application to the dot blot apparatus. After dot blotting, the membrane is briefly placed on absorbent paper to draw off excess liquid. The membrane is then placed inside a UV light box, such as the Stratalinker™ light box manufactured by Stratagene, and exposed to 50 to 60 millijoules/cm$^2$ of flux at 254 nm to fix the tailed probe to the nylon membrane. After a brief rinse (for about 15 minutes in hybridization solution) to remove unbound probe, the membrane is then ready for hybridization with biotinylated PCR product.

Amplified PCR products are denatured by heating to 95° C. for 3 to 10 minutes and 40 μl of the denatured PCR product are added to each probe panel for hybridization. Hybridization is carried out at 57° C. for 20 minutes in a shaking water bath in a hybridization buffer composed of 0.5X SSPE, 0.25% SDS, and 5X Denhardt's solution (20X SSPE contains 0.02 M EDTA, 0.2 M NaH$_2$PO$_4$, 3.6 M NaCl; 0.11 M NaOH, adjusted to pH 7.4). The hybridization buffer is replaced with 3 ml of a solution consisting of 25 μl of SA-HRP, commercially available from Perkin Elmer, in 3.1 ml hybridization buffer, and incubated for 20 minutes at 57° C. in a shaking water bath.

Washing is carried out in a wash buffer of 2X SSPE and 0.1% SDS. After a brief rinse of the membrane in 10 ml of wash buffer, a 12 minute stringent wash in 10 ml of buffer is done at 57° C. Another 5 minute room temperature wash is then carried out, followed by a 5 minute wash in 10 ml of 0.1 M sodium citrate, pH 5.0.

Chromogen binding is carried out in 5 ml of chromogen solution consisting of 5 ml of 0.1 M sodium citrate, 5 μl of 3% hydrogen peroxide, and 0.25 ml chromogen (TMB from Perkin Elmer) for 25–30 minutes at room temperature. Three 10 minute washes in distilled water are carried out at room temperature. A post-wash of 1X PBS at room temperature for 30 minutes can enhance signal quality. During these steps involving the chromogen, the membrane should be shielded from light by an aluminum foil covering. The developed membrane should be photographed for a permanent record.

EXAMPLE 4

Microtiter Plate Format

In this embodiment of the invention, the probe is fixed to a well of a microtiter plate. The amplified target DNA is hybridized to the bound probe as described above. As in the previous example, the amplification primers are biotinylated, to allow detection of amplified DNA that hybridizes to the bound probes.

The desired probes conjugated to BSA are first allowed to adsorb to the plastic surface of the individual wells. The wells are then blocked with protein, such as bovine serum albumin. Preferably, 96 well plates available from Corning are used.

Once the amplification has been completed, the PCR tubes were removed from the thermocycler (available through Perkin Elmer). One hundred microliters of denaturation solution were added to each PCR tube. A new pipette tip is used for each tube. In one embodiment, detection may not be preformed immediately. In that case, the PCR tubes were storied overnight at 2° C. to 8° C. Denatured amplification reactions become viscus upon storage at 20C. to 8° C. Tubes were briefly warmed at 25° C. to 30° C. prior to opening tubes to make pipette easy.

The appropriate number of eight well microliter plate strips (minimally 2 strips) were removed and set into the microtiter plate frame. One hundred microliters of hybridization buffer was pipetted into each well of the microtiter plate.

The denaturation solution contains 0.4 M NaOH; 80 mM EDTA and 0.005% Thymol blue. Hybridization/neutralization buffer contains: 2.5 M NaSCN; 80 mM NaH$_2$PO$_4$; 10 mM NaH$_2$PO$_4$; and 0.125% Tween 20. Before use the pH is checked to be 5.0 +/−0.2.

Using plugged tips with a multi channel pipetter, 25 μl of the denatured amplification reaction from each PCR tube in the tray was pipetted to the corresponding well position in the microtiter plate. The plate was covered with the microtiter plate lid and gently tapped on the side 10 to 15 times. Wells in which proper reagent pipetting has been done will turn light yellow in color. If no or only a single change in blue color is noted, excess amplicon has been added. The test is continued as positive OD values will increase but negative OD values are not affected. The plate was incubated for 60 minutes at 37° C.

Following incubation the plate was washed five times with wash solution. Washing of the plate may be preformed manually or with an automated microtiter plate washer programmed accordingly. For washing, a 1X PCR wash buffer was used. A 10X concentrate of PCR washed buffer was prepared as follows: 9.94 grams per liter of sodium phosphate dibasic; 4.41 grams per liter sodium phosphate (monobasic); 3.722 grams per liter EDTA; 87.66 grams per liter sodium chloride; 13.7 grams per liter of Tween 20; and 10 grams per liter of Pro Clin 300 (Rohm and Haas, Philadelphia, Pa.). The solution is pH with phosphoric acid (pH 6.5–7.1 is preferred).

For manual washing the contents of the plate were emptied and tapped dry. Three hundred microliters of wash solution was added to each well in the plate being tested, and the plate was allowed to dry for 15 to 30 seconds. The plate was again emptied and tapped dry. This wash process was repeated four additional times.

For an automated microplate washer, the following procedure was used. The contents of the wells was aspirated. The washer was programmed to add 350 microliters of working wash solution to each well in the plate being tested and soaked for 30 seconds and aspirated. The steps were repeated four additional times. The plate was then tapped dry.

One hundred microliters of conjugate was added to each well in the plate being tested. The avidin-HRP conjugate is prepared as follows. The diluent contains 0.1 molar; 0.25%

Emulsit 25 (DKS International, Inc., Tokyo, Japan); 1.0% Kathon CG (Rohm and Haas, Philadelphia, Pa.); 0.1% phenol; 1.0% bovine gamma globulin. The solution was pH to 7.3 with concentrated HCL. To this diluent 10mM of conjugated avidin was added (Vector Labs, Burlingame, Calif.). The plate was then covered and then incubated 50 minutes at 37° C. and again washed as described above. The working substrate was prepared by mixing 2.0 ml of Substrate A and 0.5 ml of Substrate B for each multiple of two 8 well microtiter plate strips (16 tests). Substrate A contains 3 mM hydrogen peroxide; 6.5 mM citrate and 0.1% Kathon CG. Substrate B contains 4.2 mM 3,3',5,5' tetramethylbenzidine and 40% dimethylformamide. The working substrate was prepared no more than three hours before use and was stored away from direct sunlight.

One hundred microliters of working substrate (substrate A and B mixture) was added to each well of the plate being tested. The plate was then covered and incubated in the dark for 10 minutes at room temperature (20° C. to 25° C.). One hundred microliters of Stop Reagent (5% $H_2SO_4$) was added to each well being tested. The absorbance of each well of 450 mM was read within one hour of adding the Stop Reagent. The absorbance value was recorded for specimen and control.

EXAMPLE 5

Probes and Primer Pairs

The oligonucleotides of the present invention provide numerous combinations of primers and probes that can be used in the amplification of HCV genomic sequences and detection of the amplified product. A large number of oligonucleotides have been tested for effectiveness as primers in an RT-PCR amplification.

PCR amplification reactions were carried out with various pairs of oligonucleotides using the methods described in Example 1. Amplified product was detected by standard methods of agarose gel electrophoresis separation and staining (see Sambrook et al., *supra*). Each of the upstream primers KY65 (SEQ ID NO. 1) and KY98 (SEQ ID NO. 3) functioned effectively with each of the downstream primers KY68 (SEQ ID NO. 27), KY95 (SEQ ID NO.20), and KY99 (SEQ ID NO. 26) in the amplification of HCV sequences. KY67 (SEQ ID NO. 10) functioned effectively with both KY68 (SEQ ID NO. 27) and KY99 (SEQ ID NO. 26). Each of the upstream primers KY80 (SEQ ID NO. 5), KY83 (SEQ ID NO. 7), KY84 (SEQ ID NO. 8), KY85 (SEQ ID NO. 9), and KY 144 (SEQ ID NO. 6) functioned effectively with each of the downstream primers KY78 (SEQ ID NO. 18), KY95 (SEQ ID NO. 20), KY145 (SEQ ID NO. 19), KY148 (SEQ ID NO. 17), and KY149 (SEQ ID NO. 16). Finally, each of the upstream primers KY80 (SEQ ID NO. 5) and KY81 (SEQ ID NO. 11) functioned effectively with KY100 (SEQ ID NO. 21).

Amplification product from PCR amplification using KY78 (SEQ ID NO. 18) and KY80 (SEQ ID NO. 5) as primers was detected by probing with each of KY88 (SEQ ID NO. 12), KY84 (SEQ ID NO. 8), and KY85 (SEQ ID NO. 9) using the methods described in Example 2, above.

Primers KY153 (SEQ ID NO. 5), KY149 (SEQ ID NO. 16), and KY148 (SEQ ID NO. 17) cannot be used with any of the upstream primers that are downstream of KY85. The 3'-end of KY78 (SEQ ID NO. 18) is adjacent to the 3'-end of KY88 (SEQ ID NO. 12), so although these two primers could function as a primer pair, the lack of any intervening sequence makes independent probing impossible. Primer KY86 (SEQ ID NO. 13) can only be paired with KY100 (SEQ ID NO. 21), KY99 (SEQ ID NO. 26), KY109 (SEQ ID NO. 24), and KY111 (SEQ ID NO. 25). Primer KY87 (SEQ ID NO. 14) can only be paired with KY99 (SEQ ID NO. 26), KY109 (SEQ ID NO. 24), and KY 111 (SEQ ID NO. 25).

KY84 (SEQ ID NO. 8), KY85 (SEQ ID NO. 9), KY87 (SEQ ID NO. 14), and KY148 (SEQ ID NO. 17) discussed above are useful for the detection of known HCV isolates other than the C9 isolate. The probes and primers disclosed in Table 4 are specific for amplifying and detecting HCV-C9 and related variants and for excluding Japan and U.S. HCV prototypes.

Primers for specifically amplifying Japan and U.S. HCV prototypes and not HCV-C9 are exemplified by KY84 (SEQ ID NO. 8), KY85 (SEQ ID NO. 9), KY148 (SEQ ID NO. 17) and KY87 (SEQ ID NO. 14). Primers for amplifying Japan, U.S., and C9 HCV prototypes include KY67 (SEQ ID NO. 10), KY78 (SEQ ID NO. 18), KY80 (SEQ ID NO. 5), KY81 (SEQ ID NO. 11 ), KY83 (SEQ ID NO. 7), KY86 (SEQ ID NO. 13), KY88 (SEQ ID NO. 12), KY95 (SEQ ID NO. 20), KY100 (SEQ ID NO. 21), KY144 (SEQ ID NO. 6), KY145 (SEQ ID NO. 19), and KY153 (SEQ ID NO. 15). Primers KY65 (SEQ ID NO. 1), KY68 (SEQ ID NO. 27), KY98 (SEQ ID NO. 3), KY99 (SEQ ID NO. 26), KY109 (SEQ ID NO. 24), KY111 (SEQ ID NO. 25), and KY149 (SEQ ID NO. 16) are suitable for amplifying Japan and U.S. HCV prototype and related variant isolates and may be suitable for detecting HCV-C9 and related isotypes as well.

Probes for detecting Japan, U.S., and C9 HCV prototypes and related variants are exemplified by KY67 (SEQ ID NO. 10), KY78 (SEQ ID NO. 18), KY81 (SEQ ID NO. 11), KY86 (SEQ ID NO. 13), KY95 (SEQ ID NO. 20), KY150 (SEQ ID NO. 43), and KY 145 (SEQ ID NO. 19). Probes for detecting Japan and U.S. HCV prototype and related variants which probes do not detect the HCV-C9 prototype include KY83 (SEQ ID NO. 7), KY87 (SEQ ID NO. 14), KY84 (SEQ ID NO. 8), KY88 (SEQ ID NO. 12), KY85 (SEQ ID NO. 9), KY100 (SEQ ID NO. 21), KY148 (SEQ ID NO. 17), and KY149 (SEQ ID NO. 16). Probes KY65 (SEQ ID NO. 1), KY68 (SEQ ID NO. 27), KY82 (SEQ ID NO. 28), KY99 (SEQ ID NO. 26), KY109 (SEQ ID NO. 24), KY111 (SEQ ID NO. 25), KY80 (SEQ ID NO. 5), KY144 (SEQ ID NO. 6), and KY153 (SEQ ID NO. 15) are suitable for detecting Japan and U.S. HCV prototype and related variant isolates and may be suitable for detecting HCV-C9 and related variants as well.

EXAMPLE 6

A Preferred Methods for Homogeneous RT/PCR Amplification of HCV RNA in the Presence of UNG The homogeneous RT-PCR amplification method described in Example 1 was modified to include a sterilization step. The protocol described below demonstrates that the RT and PCR reactions incorporate dUTP. Sterilization occurs at 50° C. prior to the RT step. At the elevated RT-PCR reaction temperatures UNG is inactive, and the dU containing products are not degraded. Two units of UNG (Perkin Elmer) successfully sterilized a carryover equivalent to 0.25 µl of a 100 µl amplification made with 10,000 copies of HCV RNA. Higher amounts of UNG, for example, up to 6 units per 100 µl reaction, are also suitable.

| Reaction Mix Components Were Added in the Following Order | μl/Rx |
|---|---|
| 50% Glycerol | 16.00 |
| 10X RT Rxn. Buffer (100 mM Tris-HCl (pH 8.3), 900 mM KCl) | 10.00 |
| dGTP (10 mM); 200 μM final | 2.00 |
| dATP (10 mM); 200 μM final | 2.00 |
| dUTP (20 mM); 200 μM final | 1.00 |
| dCTP (10 mM); 200 μM final | 2.00 |
| KY80 (SEQ ID NO. 5) at 15 μM (15 pmoles each/rxn final); (+) biotinylated strand primer | 1.00 |
| KY78 (SEQ ID NO. 18) at 15 μM (15 pmoles each/rxn final); biotinyl. (−) strand, RT primer | 1.00 |
| UNG: 1 unit/μl | 2.00 |
| rTth DNA polymerase: 2.5 U/μl in 1X enzymer storage buffer* | 4.00 |
| MnCl₂ (10 mM); 0.9 mM final | 9.00 |
| Master Mix per tube | 50.00 |
| RNA (with carrier background** in H₂O) | 50.00 |
| TOTAL VOLUME OF REACTION | 100.00 |

*1X enzyme storage buffer = (20 mM Tris-HCl [pH 7.5], 100 mM KCl, 0.1 mM EDTA, 1 mM DTT, 0.5% Tween 20 [Pierce Surfactamps], 50% glycerol [v/v]).
**1 μg poly rA homopolymeric RNA from Pharmacia (#27-4110) per reaction is routinely used and up to 2 μg is tolerated. The poly rA has an average $S_{20,w}$ of 8.8 (Range 6–13) or approximately 100–400 nt. Heterologous DNAs seems to give rise to some non-specific products at the annealing temperature used at input levels of less than 200 ng per reaction. Calf thymus DNA, PBL DNA, human placental DNA, and DNA from the cell line K562 have been examined and behave similarly.

Procedure

1. Turn on TC9600 thermocycler to preheat cover.
2. Prepare reaction mix at room termperature.
3. Place tubes into thermocycler and press "Run" to restart thermocycler.
4. Start machine at file 8.
5. Suggested thermocycle conditions:

| File 1: Hold | 2 min. at 50° C. | UNG Sterilization Step |
|---|---|---|
| File 2: Hold | 15 min. at 70° C. | Reverse Transcription Step |
| File 3: Hold | 1 min. at 95° C. | |
| File 4: Two Temp. PCR | 15 sec. at 95° C. and 10–30 sec. at 60° C. for 2 cycles | |
| File 5: Two Temp. PCR | 15 sec. at 90° C. and 10–30 sec. at 60° C. for 38 cycles | |
| File 6: Hold | 72° C. for 1 hour | |
| File 7: Hold | 15° C. indefinitely | |
| File 8: Link | Files: 1, 2, 3, 4, 5, 6, and 7 | |

At step 5, file 2, the 15 min. reaction time can be lowered to 5 minutes without decreasing the reaction efficiency. At step 5, file 5, for high G+C templates, it may be preferable to raise the denaturation temperature to 95° C. Analysis of reaction products by microtiter plate assay format generally resulted in absorbance values greater than 0.8 for positive samples and ≦0.5 for negative samples.

We claim:

1. An oligonucleotide probe for detecting hepatitis C virus (HCV) nucleic acid from a Japan or U.S. isolate, wherein said probe consists of a nucleic acid sequence at least 14 nucleotides in length contained in a region of HCV genomic nucleic acid corresponding to SEQ ID NO: 29, wherein said nucleic acid sequence is specific to said Japan and U.S. isolates and is not specific to a C9 isolate.

2. An oligonucleotide probe for detecting hepatitis C virus (HCV) nucleic acid from a C9 isolate, wherein said probe consists of a nucleic acid sequence at least 14 nucleotides in length contained in a sequence selected from the group consisting of SEQ ID NO: 29, SEQ ID NO: 30, SEQ ID NO: 31, SEQ ID NO: 32, SEQ ID NO: 33, and the complements thereof, wherein said nucleic acid sequence is specific to a C9 isolate.

3. An oligonucleotide probe for detecting hepatitis C virus (HCV) nucleic acid, wherein said probe consists of a nucleic acid sequence at least 14 nucleotides in length contained in a sequence selected from the group consisting of SEQ ID NO: 29, SEQ ID NO: 30, SEQ ID NO: 31, SEQ ID NO: 32, SEQ ID NO: 33, and the complements thereof, wherein said nucleic acid sequence is specific to Japan, U.S., and C9 isolates.

\* \* \* \* \*